United States Patent
Yasuda et al.

(10) Patent No.: US 10,168,267 B2
(45) Date of Patent: Jan. 1, 2019

(54) ROTATIONAL SPEED DETECTION DEVICE, VISCOSITY MEASUREMENT DEVICE USING THE DEVICE, ROTATIONAL SPEED DETECTION METHOD, AND ROTATING OBJECT USED IN THE METHOD

(71) Applicant: KYOTO ELECTRONICS MANUFACTURING CO., LTD., Kyoto-shi, Kyoto (JP)

(72) Inventors: Masanori Yasuda, Kyoto (JP); Keiji Sakai, Tokyo (JP)

(73) Assignee: KYOTO ELECTRONICS MANUFACTURING CO., LTD., Kyoto (JP)

( * ) Notice: Subject to any disclaimer, the term of this patent is extended or adjusted under 35 U.S.C. 154(b) by 25 days.

(21) Appl. No.: 14/903,678

(22) PCT Filed: Jul. 1, 2014

(86) PCT No.: PCT/JP2014/067526
§ 371 (c)(1),
(2) Date: Jan. 8, 2016

(87) PCT Pub. No.: WO2015/012071
PCT Pub. Date: Jan. 29, 2015

(65) Prior Publication Data
US 2016/0161387 A1    Jun. 9, 2016

(30) Foreign Application Priority Data

Jul. 23, 2013 (JP) ................................. 2013-152446

(51) Int. Cl.
*G01N 11/14* (2006.01)
*G01P 3/36* (2006.01)
(Continued)

(52) U.S. Cl.
CPC ............... *G01N 11/14* (2013.01); *G01P 3/36* (2013.01); *G01P 3/80* (2013.01); *G01N 2011/008* (2013.01); *G02B 27/48* (2013.01)

(58) Field of Classification Search
CPC ........................................................ G01P 3/36
See application file for complete search history.

(56) References Cited

U.S. PATENT DOCUMENTS 3,419,330 A * 12/1968 Schneider .............. G01C 19/28
356/28.5
3,804,518 A * 4/1974 Meyr ...................... G01P 3/806
324/175

(Continued)

FOREIGN PATENT DOCUMENTS

JP           519552       3/1976
JP    WO 2012157572 A1 *  11/2012  ............. G01N 11/14

OTHER PUBLICATIONS

PCT/JP2014/067526; PCT International Search Report of the International Searching Authority dated Jul. 16, 2014 and its English translation.

(Continued)

*Primary Examiner* — John Fitzgerald
*Assistant Examiner* — Alexander A Mercado
(74) *Attorney, Agent, or Firm* — Renner, Otto, Boisselle & Sklar, LLP

(57) ABSTRACT

A rotational speed detection device is provided that can detect the rotational speed of a rotating object with high precision by readily controlling a relatively inexpensive and compact optical device, and has a lower cost and a smaller size with maintained or improved detection precision of the rotational speed of the rotating object. The rotational speed detection device includes a light emitting unit (5), a light receiving unit (6), a received light data obtaining unit (13), and a rotational speed calculation unit (15) that calculates (Continued)

the rotational speed of a rotating object (3). The rotating object (3) has an irregular uneven portion (3A) on a rotating surface thereof. The received light data obtaining unit (13) obtains time-series data of received light data of light reflected by the uneven portion (3A). The rotational speed calculation unit (15) calculates the rotational speed of the rotating object (3) from the periodicity of the time-series data.

14 Claims, 11 Drawing Sheets

(51) Int. Cl.
*G01P 3/80* (2006.01)
*G01N 11/00* (2006.01)
*G02B 27/48* (2006.01)

(56) References Cited

U.S. PATENT DOCUMENTS

| | | | | |
|---|---|---|---|---|
| 3,895,872 A * | 7/1975 | Dandliker | G01F 1/661 | 356/28 |
| 4,104,489 A * | 8/1978 | Satoh | G11B 7/0065 | 359/29 |
| 4,204,115 A * | 5/1980 | Boldridge, Jr. | G01D 5/347 | 250/227.11 |
| 4,387,785 A * | 6/1983 | Fromm | G01H 9/006 | 181/142 |
| 4,435,080 A * | 3/1984 | Maly | G01N 11/142 | 356/337 |
| 4,525,068 A * | 6/1985 | Mannava | G01P 3/366 | 356/28.5 |
| 4,551,017 A * | 11/1985 | Mannava | G01P 3/366 | 356/28.5 |
| 4,551,018 A * | 11/1985 | Mannava | G01P 3/366 | 356/28.5 |
| 5,011,278 A * | 4/1991 | Farrell | G01P 5/001 | 356/28 |
| 5,054,913 A * | 10/1991 | Ishikawa | G01P 5/001 | 250/233 |
| 5,214,278 A * | 5/1993 | Banda | G01D 5/268 | 250/231.13 |
| 5,365,787 A * | 11/1994 | Hernandez | G01H 1/003 | 324/207.25 |
| 5,612,544 A * | 3/1997 | Busch | G01P 3/486 | 235/462.08 |
| 5,636,014 A | 6/1997 | Hanson | | |
| 5,701,172 A * | 12/1997 | Azzazy | G01P 5/26 | 356/28 |
| 6,167,752 B1 * | 1/2001 | Raffer | G01N 11/142 | 73/54.28 |
| 6,233,045 B1 * | 5/2001 | Suni | G01C 3/08 | 356/28.5 |
| 6,248,994 B1 * | 6/2001 | Rose | G01B 11/162 | 250/231.13 |
| 2002/0093878 A1 * | 7/2002 | Steinberg | B01F 3/10 | 366/315 |
| 2003/0137648 A1 * | 7/2003 | Van Voorhis | G01P 3/36 | 356/28.5 |
| 2007/0193343 A1 * | 8/2007 | Liberatore | G01N 11/14 | 73/54.33 |
| 2007/0266776 A1 * | 11/2007 | Liberatore | G01N 11/142 | 73/54.23 |
| 2011/0036150 A1 | 2/2011 | Sakai | | |
| 2014/0047903 A1 * | 2/2014 | Sakai | G01N 11/14 | 73/54.28 |
| 2014/0165710 A1 | 6/2014 | Yasuda et al. | | |

OTHER PUBLICATIONS

Extended European Search Report issued for the European patent Application No. 14828960.6 dated Jan. 5, 2017.
First Office Action issued for Japanese Patent Application No. 2015-528206 dated Apr. 4, 2017 and it's English translation.
Offical Action for Chinese Patent Application No. 201480041228.3 dated Feb. 24, 2018 and its English translation.

* cited by examiner

ROTATIONAL SPEED DETECTION DEVICE, VISCOSITY MEASUREMENT DEVICE USING THE DEVICE, ROTATIONAL SPEED DETECTION METHOD, AND ROTATING OBJECT USED IN THE METHOD The present application is a U.S. National Stage Application based on and claiming benefit of and priority under 35 U.S.C. § 371 to International Application No. PCT/JP2014/067526, filed 01 Jul. 2014, which in turn claims benefit of and priority to Japanese Application No. 2013-152446, filed 23 Jul. 2013, the entirety of each of which is hereby incorporated herein by reference.

TECHNICAL FIELD

The present invention relates to a rotational speed detection device including a rotating object, a light emitting unit that emits light to the rotating object, a light receiving unit that receives light that is emitted from the light emitting unit to the rotating object and then reflected by the rotating object, a received light data obtaining unit that obtains received light data of light received by the light receiving unit, and a rotational speed calculation unit that calculates a rotational speed of the rotating object based on the received light data obtained by the received light data obtaining unit, a viscosity measurement device using the rotational speed detection device, a rotational speed detection method, and a rotating object used in the method.

BACKGROUND ART

Among conventional rotational speed detection devices is, for example, a number-of-revolutions measurement device described in Patent Document 1 that includes a rotator, an image capture element that captures an image of a mark attached to the rotator, and an image processing unit that processes the image captured by the image capture element, and is configured to detect the rotation of the rotator mark using the image processing unit and thereby measure the number of revolutions of the rotator. In addition to the measurement of the number of revolutions of the rotor using the image capture element, Patent Document 1 also describes an alternative technique of measuring the number of revolutions by emitting laser to a rotator and then optically measuring a change in pattern of reflection or interference caused by rotation.

Patent Document 2 also describes a similar number-of-revolutions measurement device that includes a rotator, a CCD camera that captures an image of a mark attached to the rotator, and an image processing unit that processes the image captured by the CCD camera, and measures the number of revolutions of the rotator by detecting the rotator mark using the image processing unit. Patent Document 2 also states that a light emitting unit that emits laser light to the rotator and a light receiving unit that receives the laser light reflected by the rotator are provided, and the number of revolutions is detected by detecting a change in pattern of reflection or interference caused by the rotation of the rotator using a number-of-revolutions detection unit.

CITATION LIST

Patent Literature

Patent Document 1: Japanese Unexamined Patent Application Publication No. 2009-264982 (see, particularly, paragraphs [0019], [0023], and [0045])

Patent Document 2: International Publication WO2013/015211 (see, particularly, paragraphs [0024] and [0033]-[0036])

SUMMARY OF INVENTION

Technical Problem

However, the techniques of measuring the number of revolutions by performing image processing on the mark attached on the rotator, that are described in Patent Documents 1 and 2, are practical, but it is necessary to perform, for example, advanced image processing using an expensive image capture means, such as a CCD camera or the like, which causes problems, such as an increase in manufacturing cost of the number-of-revolutions measurement device, an increase in size of the number-of-revolutions measurement device, and the like. Also, when an image of the mark attached to the rotator is captured using a CCD camera or the like, the captured image is likely to be unclear due to the influence of chromatic aberration, and it is difficult to accurately detect a change in luminance due to the influence of external disturbing light or the like, for example. For these reasons, it is also difficult to detect the number of revolutions of the rotator with high precision.

Patent Documents 1 and 2 also describe the techniques of measuring the number of revolutions of the rotator using an optical means. However, when the rotator, which has a smooth surface, is illuminated with laser light, the light reflected by the surface has a uniform intensity distribution, and therefore, has substantially no characteristic pattern change, or a characteristic pattern change with considerably low intensity if any. Therefore, it is difficult to detect the number of revolutions of the rotator. Such optical techniques are a long way from practical use.

It is an object of the present invention to provide a rotational speed detection device that can detect the rotational speed of a rotating object with high precision by readily controlling a relatively inexpensive and compact optical device, and has a lower cost and a smaller size with maintained or improved detection precision of the rotational speed of the rotating object.

Solution to Problem

The present inventors conceived, through trial and error, that the rotational speed of a rotating object could be readily detected by effective use of the nature of a so-called speckle. This conception encouraged the present inventors to repeatedly perform, for example, analysis of various received light data, to make the present invention. Configurations, operations, and advantages of the present invention will now be described.

A first invention is directed to a rotational speed detection device including a rotating object, a light emitting unit of emitting light to the rotating object, a light receiving unit of receiving light reflected by the rotating object after being emitted from the light emitting unit to the rotating object, a received light data obtaining unit of obtaining received light data of the light received by the light receiving unit, and a rotational speed calculation unit of calculating a rotational speed of the rotating object based on the received light data received by the received light data obtaining unit. The rotating object has a rotating surface, and an irregular uneven portion on the rotating surface, the uneven portions having projections and depressions. The received light data obtaining unit obtains time-series data of received light data of light reflected by the uneven portion. The rotational speed calculation unit calculates the rotational speed of the rotating object from periodicity of the time-series data.

According to the above configuration, when the irregular uneven portion is illuminated with light from the light emitting unit, light waves reflected from different points on the irregular uneven portion interfere with each other, resulting in irregular received light data of light received by the light receiving unit. Thereafter, the received light data obtaining unit obtains time-series data of the received light data. Time-series data having periodicity corresponding to the rotation of the rotating object emerges from the irregular received light data. The rotational speed calculation unit can precisely and readily calculate the rotational speed of the rotating object from the periodicity of the time-series data. As a result, the rotational speed of the rotating object can be detected with high precision by a simple control using a relatively inexpensive and compact optical device without performing, for example, advanced image processing using an expensive and large image capture means. Moreover, for example, even if the rotational speed of the rotating object is high, the periodicity of the time-series data is maintained, and therefore, the rotational speed of the rotating object that rotates at high speed can be detected with high precision. In this case, the uneven portion on the rotating surface of the rotating object can be relatively easily formed by, for example, a surface treatment or the like, and therefore, the manufacturing cost of the rotating object does not significantly increase.

Therefore, the manufacturing cost of the rotational speed detection device can be reduced while the detection precision of the rotational speed of the rotating object is maintained or improved, resulting in a smaller rotational speed detection device.

A second invention is directed to the rotational speed detection device of the first invention, in which, in the uneven portion, a distance between bottom portions of adjacent depressions and a distance between top portions of adjacent projections have a length that is one hundredth or less of a maximum perimeter of the rotating object, and is ten times or more a wavelength of the light emitted by the light emitting unit.

According to the above configuration, the received light data of light received by the light receiving unit is likely to have significant intensity changes, and therefore, the periodicity of the time-series data can be more clearly detected. As a result, the rotational speed of the rotating object can be calculated with higher precision.

A third invention is directed to the rotational speed detection device of the first or second invention, in which the uneven portion is formed on the rotating surface of the rotating object by surface abrasion or polishing.

According to the above configuration, the uneven portion can be readily formed on the rotating surface of the rotating object by changing conditions for abrading or polishing the rotating surface of the rotating object. Specifically, for example, a predetermined uneven portion can be readily formed by abrading or polishing the rotating surface of the rotating object so that the rotating surface of the rotating object becomes slightly rougher than specular surface. Also, if the uneven portion is formed by surface abrasion or polishing, the uneven portion does not disappear or come off during detection of the rotational speed, unlike a mark attached to the rotating surface of the rotating object, for example.

A fourth invention is directed to the rotational speed detection device of any one of the first to third inventions, in which the light receiving unit includes a single light receiving unit, the received light data obtaining unit obtains the time-series data corresponding to one or more revolutions of the rotating object, and the rotational speed calculation unit measures a time it takes for the rotating object to rotate one revolution, from the time-series data corresponding to one or more revolutions of the rotating object, and calculates the rotational speed of the rotating object from the time.

According to the above configuration, the rotational speed of the rotating object can be calculated with high precision by using a simple device configuration including a single light receiving unit, and performing a simple control, i.e., only measuring a time it takes for the rotating object to rotate one revolution and calculating the rotational speed.

A fifth invention is directed to the rotational speed detection device of the fourth invention, in which the light receiving unit has a plurality of light receiving elements facing the rotating surface of the rotating object illuminated by the light emitting unit, and aligned in a direction perpendicular to a direction of rotation of the rotating object, and the received light data obtaining unit evaluates the overall received light data detected from the plurality of light receiving elements to obtain the time-series data.

According to the above configuration, time-series data precisely corresponding to the intensity of reflected light can be obtained, and the periodicity of the time-series data can be more clearly detected.

A sixth invention is directed to the rotational speed detection device of any one of the first to third inventions, in which the light receiving unit includes an upstream light receiving unit provided upstream in a direction of rotation of the rotating object, and a downstream light receiving unit provided downstream in the direction of rotation, the received light data obtaining unit simultaneously obtains time-series data of the received light data of both the upstream and downstream light receiving units, and the rotational speed calculation unit calculates the rotational speed of the rotating object from the time-series data simultaneously obtained by both the upstream and downstream light receiving units.

According to the above configuration, if time-series data is simultaneously obtained from both the upstream and downstream light receiving units, data similar to the time-series data of the upstream light receiving unit appears as the time-series data of the downstream light receiving unit with a time difference. This phenomenon can be effectively utilized to calculate the rotational speed of the rotating object.

A seventh invention is directed to the rotational speed detection device of the sixth invention, in which the received light data obtaining unit obtains the time-series data corresponding to less than one revolution of the rotating object, and the rotational speed calculation unit calculates the rotational speed of the rotating object from the time-series data corresponding to less than one revolution of the rotating object, and an arrangement angle of the upstream and downstream light receiving units around a rotational axis of the rotating object.

According to the above configuration, the time-series data can be quickly obtained, and the rotational speed of the rotating object can be quickly calculated. Also, the above phenomenon can be effectively utilized to readily calculate the rotational speed of the rotating object from the time-series data of the upstream and downstream light receiving units and the arrangement angle of the upstream and downstream light receiving units.

An eighth invention is directed to the rotational speed detection device of the seventh invention, in which the rotational speed detection device has an angle calculation unit of calculating the arrangement angle, and an angle storage unit of storing the arrangement angle calculated by the angle calculation unit, the received light data obtaining unit obtains the time-series data of the received light data corresponding to one or more revolutions of the rotating object, as time-series data for angle calculation, the angle calculation unit calculates the arrangement angle from the time-series data for angle calculation, and the rotational speed calculation unit calculates the rotational speed of the rotating object from the arrangement angle calculated by the angle calculation unit and stored in the angle storage unit.

According to the above configuration, even if the upstream and downstream light receiving units are not accurately positioned, the arrangement angle of the upstream and downstream light receiving units can be accurately calculated by a simple operation. As a result, the rotational speed of the rotating object can be calculated using the arrangement angle with higher precision.

A ninth invention is directed to a viscosity measurement device including the rotational speed detection device of any one of the first to eighth inventions. The viscosity measurement device includes a sample container of containing a sample whose viscosity is to be measured, and the rotating object, a magnet of applying a rotating magnetic field to the rotating object from outside of the sample container, a rotation control unit of controlling a rotational speed of the rotating magnetic field, and a viscosity calculation unit of calculating the viscosity of the sample. The viscosity calculation unit calculates the viscosity of the sample using the rotational speed of the rotating object calculated by the rotational speed calculation unit, and the rotational speed of the rotating magnetic field.

According to the above configuration, the viscosity of a sample can be calculated with high precision using the rotational speed of the rotating object that is detected by the rotational speed calculation unit with high precision. Also, the manufacturing cost and size of the rotational speed detection device that is a component of the viscosity measurement device, can be reduced, resulting in a reduction in the manufacturing cost and size of the viscosity measurement device.

A tenth invention is directed to a rotational speed detection method for emitting light to a rotating object using a light emitting unit, receiving light reflected by the rotating object using a light receiving unit, and calculating a rotational speed of the rotating object based on received light data of the light received by the light receiving unit. The method includes a received light data obtaining step of emitting light to the rotating object having a rotating surface and an irregular uneven portion on the rotating surface, the uneven portion having projections and depressions, and obtaining time-series data of received light data of light reflected by the uneven portion of the rotating object, and a rotational speed calculation step of calculating the rotational speed of the rotating object from periodicity of the time-series data.

According to the above configuration, advantages similar to those of the first invention are achieved, and the rotational speed of the rotating object can be detected with high precision by a simple control using a relatively inexpensive and compact optical device.

An eleventh invention is directed to a rotating object used in the rotational speed detection method of the tenth invention, in which, in the uneven portion, a distance between bottom portions of adjacent depressions and a distance between top portions of adjacent projections have a length that is one hundredth or less of a maximum perimeter of the rotating object, and is ten times or more a wavelength of the light emitted by the light emitting unit.

According to the above configuration, advantages similar to those of the second invention are achieved, and the rotational speed of the rotating object can be calculated with higher precision.

DESCRIPTION OF EMBODIMENTS

[First Embodiment]

Figure 1:
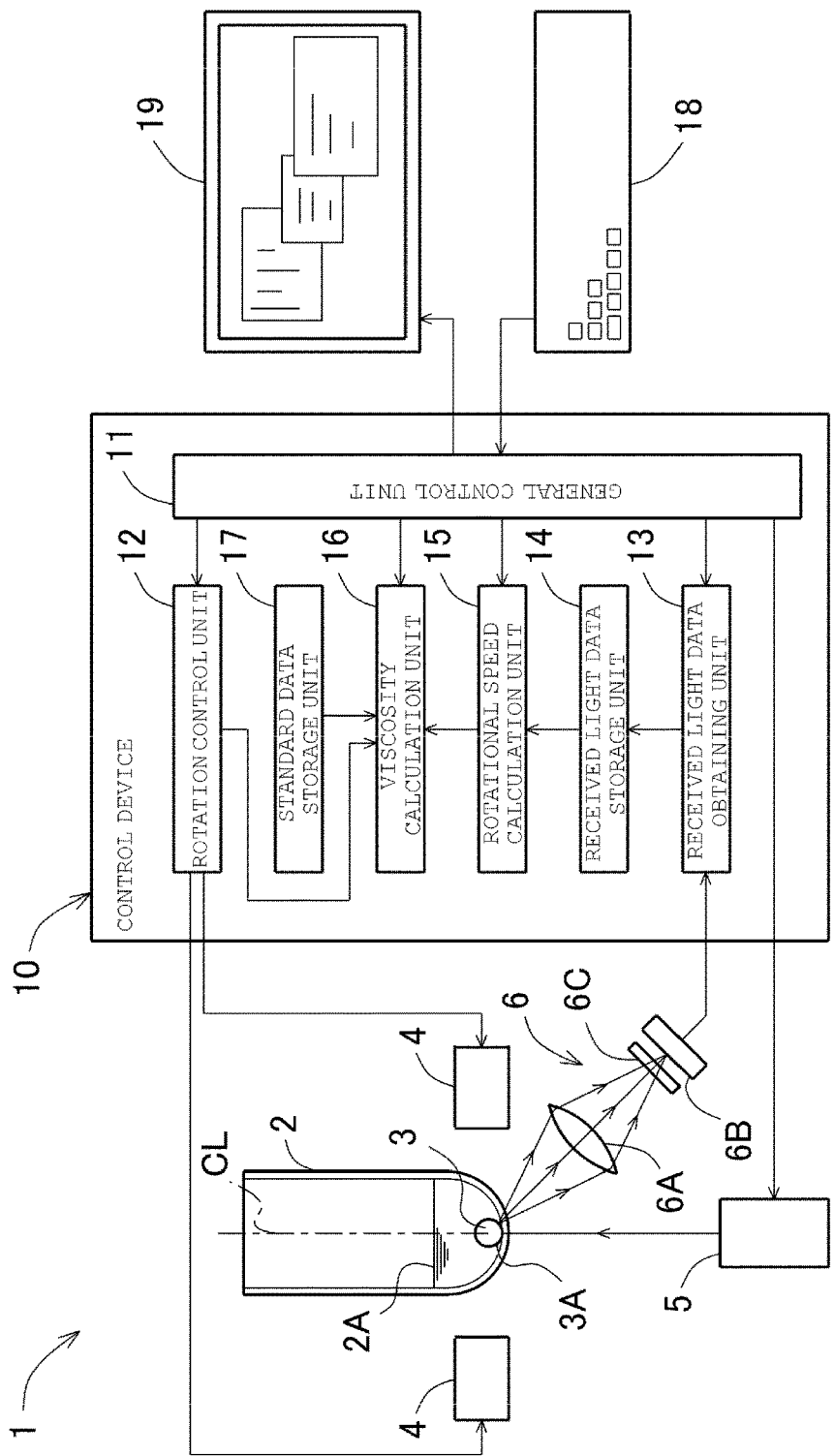
FIG. 1 is a block diagram showing an entire structure of a viscosity measurement device according to a first embodiment.

A viscosity measurement device 1 according to a first embodiment will be described with reference to FIGS. 1-4. In the first embodiment, a rotational speed detection device according to the present invention is, for example, applied to calculation of a viscosity η by the viscosity measurement device 1. As shown in FIG. 1, the viscosity measurement device 1 includes a sample container 2 that contains a substance that is a sample 2A, a rotating object 3 that is put in the sample container 2 together with the sample 2A, a plurality of electromagnets 4 that apply a rotating magnetic field to the rotating object 3 so that the rotating object 3 is rotated, a light emitting unit 5 that emits light to the rotating object 3 in the sample container 2, a light receiving unit 6 that receives light that is emitted from the light emitting unit 5 to the rotating object 3 and then reflected by the rotating object 3, and a control device 10 that controls the plurality of electromagnets 4, the light emitting unit 5, and the light receiving unit 6. In the viscosity measurement device 1, various substances are put as the sample 2A in the sample container 2. Therefore, the single viscosity measurement device 1 can be used to measure the viscosities η of a wide variety of substances ranging from the viscosities η of low-viscosity substances, such as water, blood, organic solvents, beverages, and the like, to the viscosities η of high-viscosity substances, such as polymer materials, asphalt, heavy oils, and the like.

The sample container 2 is preferably a heat-resistant container of a transparent or translucent material that can transmit light emitted from the light emitting unit 5. In the first embodiment, the sample container 2 is a glass test tube with its open end facing upward. The rotating object 3 is formed from a metal conductive material. In the first embodiment, the rotating object 3 is an aluminum sphere having a radius of curvature smaller than the radius of curvature of a bottom inner surface of the test tube that is the sample container 2. As a result, when the rotating object 3 is put in the sample container 2 together with the sample 2A, the rotating object 3 sinks in the sample 2A due to its weight and is spontaneously positioned at a center of a bottom portion of the sample container 2.

The plurality of electromagnets 4 are arranged around a lower portion of the sample container 2, including a pair of electromagnets 4 and 4 shown in FIG. 1, and a pair of electromagnets 4 and 4 (not shown) provided in front of and behind the drawing paper of FIG. 1. The electromagnets 4 and 4 in each of the two pairs face each other with the rotating object 3 being interposed therebetween. The two pairs of electromagnets 4 and 4 apply a magnetic field to the rotating object 3 from the outside of the sample container 2 to drive the rotating object to rotate about a vertical rotation axis CL.

The light emitting unit 5 functions as a light source that emits light to the rotating object 3 in the sample container 2. In the first embodiment, the light emitting unit 5 includes a laser light source that emits monochromatic light (e.g., green or yellow) so that the influence of chromatic aberration is removed and the contrast of the light is emphasized. The light emitting unit 5 is provided directly below on the rotating object 3, i.e., on an extension of the rotation axis CL of the rotating object 3, so that the optical axis of the light coincides or substantially coincides with the rotation axis CL of the rotating object 3. The light emitting unit 5 is configured to emit light having a spot diameter that is greater than or equal to a predetermined length. A circular region of a lower surface of the rotating object 3, that has its center at the rotation axis CL of the rotating object 3, is illuminated with light emitted from the light emitting unit 5.

The light receiving unit 6 includes a lens 6A that images light that is emitted from the light emitting unit 5 to the rotating object 3 and then reflected by the rotating object 3, and a photodetector 6B that detects received light data of the reflected light imaged by the lens 6A. The lens 6A is positioned to face a curved surface of a lower portion of the rotating object 3 that is illuminated with light. Also, the photodetector 6B is positioned on the optical axis of the lens 6A. A filter 6C is provided between the lens 6A and the photodetector 6B. The filter 6C has a pass band in a specific color wavelength region (e.g., a green wavelength region). If light emitted by the light emitting unit 5 is in a green wavelength region, the filter 6C is configured to mainly allow reflected light in the green wavelength region to pass therethrough. As a result, reflected light from which the influence of external disturbing light has been removed without a reduction in the amount of the reflected light, can be received by the photodetector 6B with high precision.

Note that the light emitting unit 5 may include a different light source, such as a halogen lamp or the like, instead of a laser light source. Also, when the light emitting unit 5 includes a laser light source having a single wavelength or a plurality of wavelengths, the lens 6A of the light receiving unit 6 is not essentially required. For example, if predetermined received light data can be detected without imaging because of some specifications of an uneven portion 3A or some performance (the monochromicity or linearity of light) of the laser light source, the lens 6A of the light receiving unit 6 may be optionally removed. The filter 6C may also be optionally removed when the influence of external disturbing light is unlikely to occur (e.g., a darkroom is provided around the light emitting unit 5 and the light receiving unit 6, etc.).

The control device 10 includes a general control unit 11 that generally controls the viscosity measurement device 1, a rotation control unit 12, a received light data obtaining unit 13, a received light data storage unit 14, a rotational speed calculation unit 15, a viscosity calculation unit 16 that calculates the viscosity η of the sample 2A, and a standard data storage unit 17 that stores standard data for viscosity calculation.

The rotation control unit 12 magnetizes the two pairs of electromagnets 4 by causing a current to successively flow through the coils of the electromagnets 4, and thereby applies a rotating magnetic field to the rotating object 3 to drive the rotating object 3 to rotate. Specifically, one of the two pairs of electromagnets 4 and the other are alternately or simultaneously magnetized so that magnetic fields having different directions are alternately or simultaneously generated, whereby a rotating magnetic field is applied to the rotating object 3. This induces a current in the rotating object 3. The Lorentz interaction between the induced current and the magnetic field applied to the rotating object 3 applies a rotating torque to the rotating object 3, so that the rotating object 3 is rotated. The rotation control unit 12 controls the period of the alternate or simultaneous magnetization of the two pairs of electromagnets 4 according to an instruction to rotate from the general control unit 11 so that the rotating magnetic field is rotated at a number of revolutions of N0 specified by the general control unit 11.

The received light data obtaining unit 13 receives and processes the received light data of the reflected light detected by the photodetector 6B of the light receiving unit 6 according to an instruction to obtain data from the general control unit 11. The received light data received and processed by the received light data obtaining unit 13 is stored in the received light data storage unit 14. The rotational speed calculation unit 15 reads the received light data stored in the received light data storage unit 14 according to an instruction to calculate from the general control unit 11, and calculates the number of revolutions Na of the rotating object 3. The viscosity calculation unit 16 calculates the viscosity η of the sample 2A based on the number of revolutions Na of the rotating object 3 calculated by the rotational speed calculation unit 15, the standard data stored in the standard data storage unit 17, and the number of revolutions N0 of the rotating magnetic field controlled by the rotation control unit 12, according to an instruction to calculate from the general control unit 11.

The standard data storage unit 17 stores the standard data used in calculation of the viscosity η by the viscosity calculation unit 16. The standard data is obtained as follows: a standard sample having a known viscosity η is put in the sample container 2; the rotating object 3 is rotated, and the number of revolutions Na of the rotating object 3 is measured; based on the measurement result and measurement conditions, obtained is a relationship between a difference between the number of revolutions Na of the rotating object 3 and the number of revolutions N0 of the rotating magnetic field applied to the rotating object 3, and the number of revolutions Na of the rotating object 3; such measurement and the like are performed for a plurality of standard samples having different viscosities η; and the results are stored as a data map or a first-order equation. These things are already known and therefore will not be described in detail. The relationship between the difference ΔN (=N0−Na) between the number of revolutions Na of the rotating object 3 and the number of revolutions N0 of the rotating magnetic field applied to the rotating object 3, and the number of revolutions Na of the rotating object 3, is represented by a predetermined first-order equation, and the slope ΔN/Na of the first-order equation is proportional to the viscosity η. This fact is utilized. Here, the number of revolutions N0 of the rotating magnetic field is set based on conditions for viscosity measurement. Therefore, by detecting the number of revolutions Na of the rotating object 3, the viscosity η of the sample 2A can be readily calculated using the standard data.

An input unit 18 that inputs various control instructions to the control device 10, and a display unit 19 that displays the measurement result of the viscosity η or the like calculated by the control device 10, are connected to the general control unit 11. A measurer who measures the viscosity η of the sample 2A operates the input unit 18 while viewing the display unit 19 to set conditions for viscosity measurement and provide various instructions, such as an instruction to start viscosity measurement, and the like. Thereafter, the general control unit 11 automatically measures the viscosity of the sample 2A under the viscosity measurement conditions set by the measurer, and automatically displays the measurement result on the display unit 19.

Figure 2:
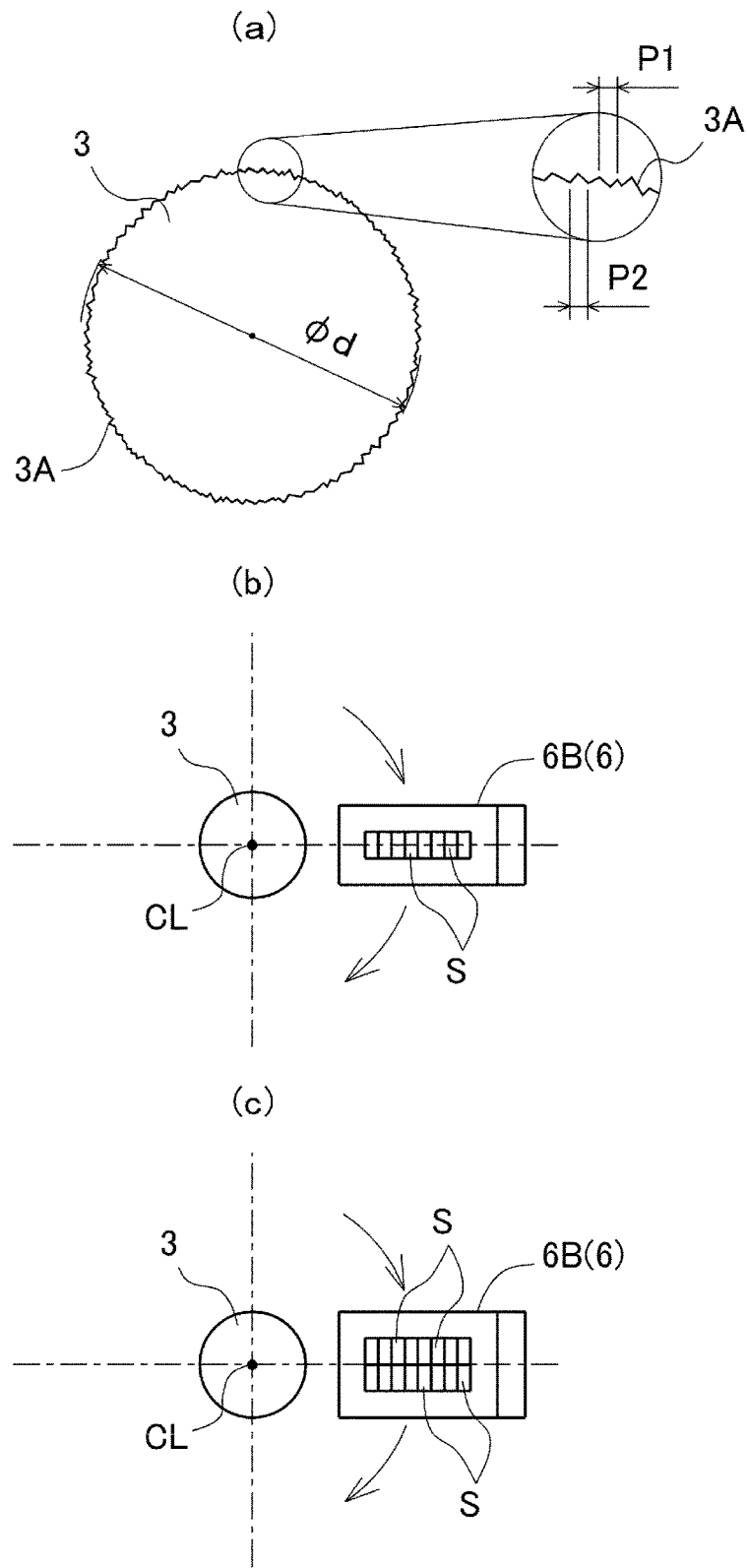
FIG. 2(*a*) is an enlarged view showing a detailed structure of a rotating object, FIG. 2(*b*) is a plan view of a photodetector, and FIG. 2(*c*) is a plan view of a photodetector according to a variation of the first embodiment.

Detailed structures of the rotating object 3 and the photodetector 6B will be described with reference to FIG. 2. As shown in FIG. 2(a), irregular and minute projections and depressions (also referred to as an uneven portion) 3A are formed on a rotating surface of the rotating object 3. The uneven portion 3A is formed throughout the rotating surface of the rotating object 3 (the entire surface of the sphere). For the uneven portion 3A, a distance P1 between top portions of adjacent projections and a distance P2 between bottom portions of adjacent depressions are set to a length that is one hundredth or less of the maximum perimeter (π×d) of the rotating object 3. Specifically, for example, when the diameter d of the rotating object 3 is 4 mm, the uneven portion 3A is formed so that the distances P1 and P2 have a length whose upper limit value is 0.13 mm or less. The present inventors repeatedly performed analysis of received light data using the viscosity measurement device 1, to find that if the distances P1 and P2 have a length that is one hundredth or less of the maximum perimeter of the rotating object 3, the periodicity of received light data (received light intensity) detected by the photodetector 6B can be reliably detected while an error is prevented from occurring in the measurement of the viscosity η due to an increase in frictional resistance between the rotating object 3 and the sample container 2. Also, for the uneven portion 3A, the distances P1 and P2 are set to have a length that is ten times or more the wavelength of light emitted from the light emitting unit 5. Specifically, for example, if the wavelength of light emitted from the light emitting unit 5 is 0.5 μm, the uneven portion 3A is formed so that the distances P1 and P2 have a length whose lower limit value is 5 μm or more. Specifically, the present inventors paid attention to the nature of speckles that a speckle pattern caused by reflected light is generated by a periodic structure (projections and depressions of a rough surface) that is larger than the wavelength of light, and repeatedly performed analysis of received light data using the viscosity measurement device 1. As a result, the present inventors found that if the rotating object 3 has a periodic structure that is ten times or more the wavelength of light emitted from the light emitting unit 5, i.e., if the distances P1 and P2 have a length that is ten times or more the wavelength of light emitted from the light emitting unit 5, significant intensity changes reliably occurs in received light data (received light intensity) detected by the photodetector 6B.

Note that when the distances P1 and P2 are set to a length that is one hundredth of the maximum perimeter of the rotating object 3, the roughness of the rotating surface of the rotating object 3 is, for example, similar to the roughness of the uneven portion 3A shown in FIG. 2(a). Also, when the distances P1 and P2 are set to a length that is ten times the wavelength of light emitted by the light emitting unit 5, the rotating surface of the rotating object 3 (not shown) is slightly rougher than specular surface. This roughness makes it difficult to determine whether projections and depressions are formed when the surface is viewed by the naked eye or a microscope, but allows significant intensity changes to reliably occur in received light data detected by the photodetector 6B.

The uneven portion 3A can be relatively readily formed by, for example, changing conditions for abrading or polishing the rotating object 3, without leading to a significant increase in cost of the rotating object 3. Note that the uneven portion 3A illustrated in the first embodiment is formed by abrading or polishing the surface, and therefore, has a saw-like profile having sharp top portions of projections and sharp bottom portions of depressions. The uneven portion 3A may have other profiles, such as, for example, a waveform-shaped profile having curved top portions of projections and curved bottom portions of depressions, a Mt. Fuji-shaped profile that is obtained by forming dimples on the surface of the rotating object 3 like a golf ball, and the like. Alternatively, instead of surface abrasion or polishing, the uneven portion 3A may be formed by other surface treatments, such as, for example, shot peening, etching, graining, and the like. Alternatively, the uneven portion 3A may be formed by providing a coating containing minute particles.

Although, in the first embodiment, the illustrated example of the uneven portion 3A has an irregular shape, size, pitch, and the like of projections and depressions, not all of these irregular characteristics need to be possessed by the uneven portion 3A, and the uneven portion 3A may have at least one of these irregular characteristics. Specifically, for example, the uneven portion 3A may have projections and depressions having a regular shape and size and an irregular pitch, or projections and depressions having a regular pitch and an irregular shape or size, or the like. Also, although, in the foregoing example, the uneven portion 3A is formed throughout the rotating surface of the rotating object 3, the uneven portion 3A may be formed on a portion of the rotating surface of the rotating object 3, like, for example, a color ball having a porka-dot pattern or striped pattern. Also, although, in the foregoing example, the uneven portion 3A is irregular on the rotating surface of the rotating object 3 even when the rotating object 3 is not rotating, i.e., is stopped, the uneven portion 3A formed on the rotating surface of the rotating object 3 may be irregular at least when the rotating object 3 is rotating. For example, the uneven portion 3A may seem to be regular, but actually irregular in a circumferential direction along which the rotating object 3 rotates, like stitching of a hardball baseball or volleyball or the like. The uneven portion 3A may be regular when the rotating object 3 is stopped, and may be irregular during rotation in a circumferential direction along which the rotating object 3 rotates, due to the way of rotating or a difference in the position illuminated with light, like dimples of a golf ball, stitching of a football, or the like.

As shown in FIG. 2(b), the photodetector 6B includes a one-dimensional photodetector (e.g., a one-dimensional photodiode array, etc.) having a plurality of light receiving elements S arranged in parallel. In the photodetector 6B, the plurality of light receiving elements S have a light receiving surface facing the rotating surface of the rotating object 3 illuminated with light, and are aligned in a direction perpendicular to the direction of rotation of the rotating object 3. The photodetector 6B, when receiving reflected light from the uneven portion 3A, outputs a photocurrent (A: ampere) that is proportional to the intensity of the reflected light, as received light data, for each of the plurality of light receiving elements S. Note that the entire photodetector 6B has dimensions of about 5 mm×15 mm×3 mm (thickness), and the light receiving surface of each light receiving element S has dimensions of about 1 mm×2 mm.

FIG. 2(c) illustrates a variation of the first embodiment. As shown in FIG. 2(c), the photodetector 6B is not limited to the one-dimensional photodetector of FIG. 2(b), and may be a two-dimensional photodetector having a plurality of light receiving elements S two-dimensionally arranged in parallel, or a zero-dimensional photodetector having a single light receiving element S (not shown). In the photodetector 6B of FIG. 2(c), the plurality of light receiving elements S have a light receiving surface facing the rotating surface of the rotating object 3 illuminated with light, and are aligned in the direction of rotation of the rotating object 3 and in a direction perpendicular to the direction of rotation of the rotating object 3. Note that, in the case of the photodetectors 6B of FIGS. 2(b) and (c), the plurality of light receiving elements S may all be configured to function as the light receiving unit 6. Alternatively, a portion of the plurality of light receiving elements S may be caused to function as the light receiving unit 6, and if a light receiving element S functioning as the light receiving unit 6 is out of order, another light receiving element S may be effectively utilized as a spare light receiving element S.

The viscosity measurement control and rotational speed detection control performed by the control device 10 will be specifically described with reference to FIGS. 3 and 4 while referring to a procedure for operating the viscosity measurement device 1. Initially, as a preliminary step for operation of the viscosity measurement device 1, the measurer places the sample 2A whose viscosity η is to be measured, together with the rotating object 3, in the sample container 2, and sets the sample container 2 in the viscosity measurement device 1. In this case, the uneven portion 3A is formed throughout the rotating surface of the rotating object 3, and therefore, even when the uneven portion 3A is not positioned with respect to a position illuminated with light emitted by the light emitting unit 5, then if the sample 2A and the rotating object 3 are only placed in the sample container 2, which is then only set in in the viscosity measurement device 1, the uneven portion 3A can be reliably illuminated with light emitted by the light emitting unit 5. Thereafter, viscosity measurement conditions are set by operating the input unit 18 while viewing the display unit 19. Examples of the viscosity measurement conditions include the number of revolutions of the rotating magnetic field, measurement temperature, and the like. In the first embodiment, a case where the number of revolutions of the rotating magnetic field is set to N0 will be described, and the other settings of the viscosity measurement conditions will not be described.

Figure 3:
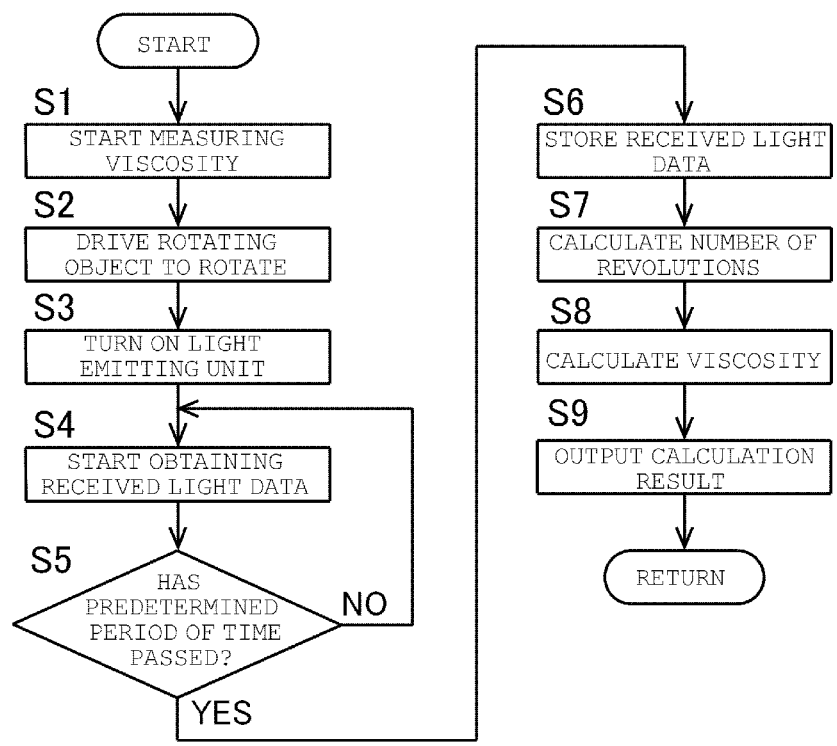
FIG. 3 is a flowchart showing details of a viscosity measurement control.
Figure 4:
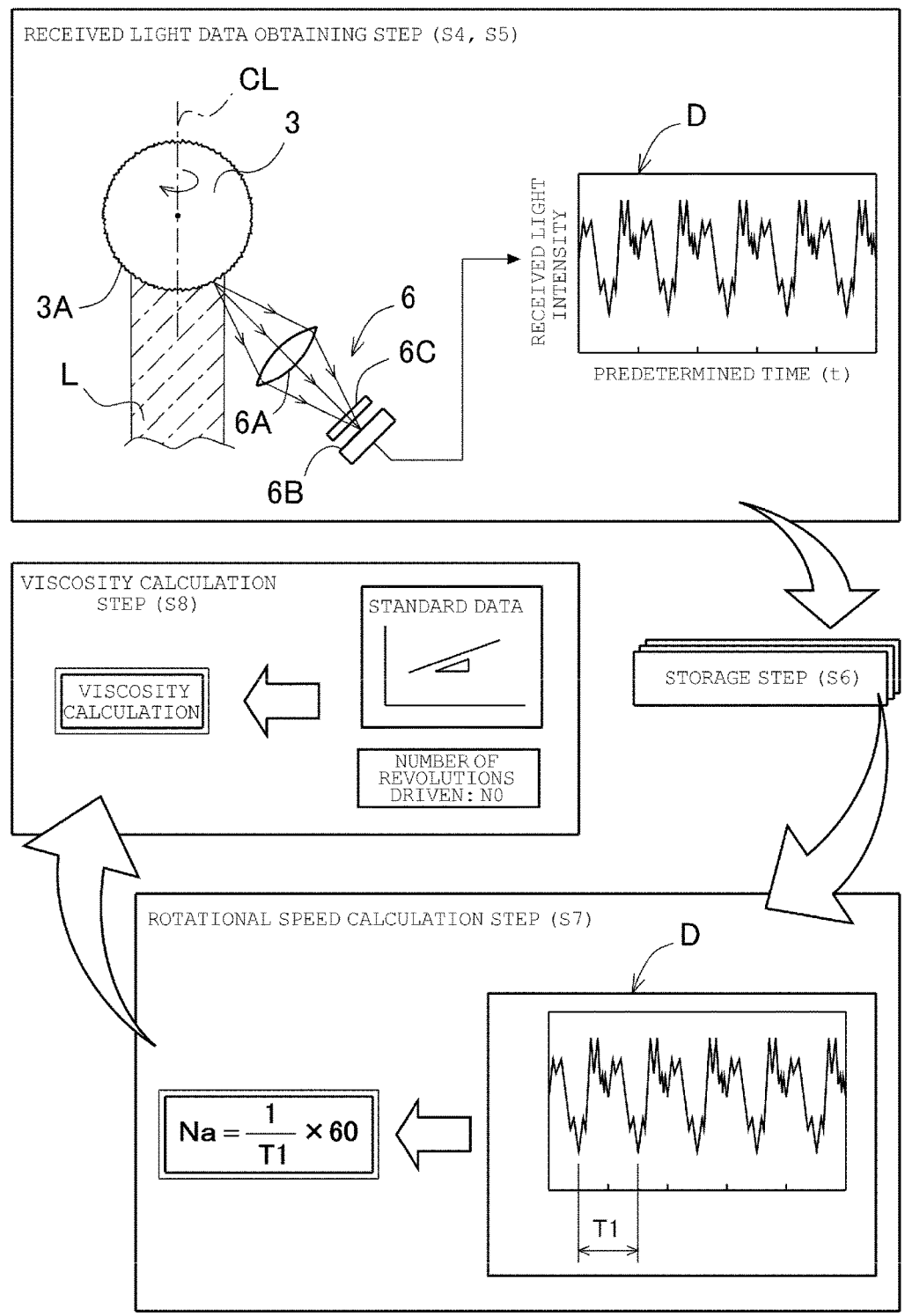
FIG. 4 is a diagram for describing details of a viscosity measurement control.

As shown in FIG. 3, after the end of the preliminary step, the measurer operates the input unit 18 to input an instruction to start viscosity measurement (step S1), and thereafter, the general control unit 11 outputs an instruction to rotate to the rotation control unit 12. Thereafter, the rotation control unit controls the period of alternate or simultaneous magnetization of the two pairs of electromagnets 4 so that the rotating magnetic field is rotated at a number of revolutions of N0 specified by the general control unit 11 (step S2). As a result, a rotating torque is applied to the rotating object 3 so that the rotating object 3 is driven to rotate. When the rotating object 3 is driven to rotate, the general control unit 11 outputs power to the light emitting unit 5 to turn on the light emitting unit 5, which then starts emitting light to the rotating object 3 in the sample container 2 (step S3). In this case, although not shown, the general control unit 11 turns on the light emitting unit 5, and outputs power to the photodetector 6B of the light receiving unit 6 to turn on the photodetector 6B. Note that the light emitting unit 5 and the photodetector 6B may be turned on at different timings. For example, the light emitting unit 5 and the photodetector 6B may be configured to be turned on when a power supply to the viscosity measurement device 1 is turned on, or when the measurer inputs an instruction to start viscosity measurement. The same applies to timings described below at which the light emitting unit 5 and the photodetector 6B are turned off.

Next, the received light data obtaining unit 13 starts obtaining received light data output from the plurality of light receiving elements S of the photodetector 6B, according to an instruction to obtain data from the general control unit 11 (step S4). The received light data obtaining unit 13 obtains received light data from input data received from the photodetector 6B at preset predetermined short time intervals. The received light data obtaining unit 13 calculates an average value of the received light data from the plurality of light receiving elements S at the preset predetermined short time intervals, and obtains the average value as the intensity of reflected light (received light intensity). Thus, the overall received light data of the plurality of light receiving elements S is evaluated to obtain the received light intensity, and therefore, time-series data D precisely corresponding to the intensity of reflected light can be obtained. Note that the received light intensity may be calculated from the received light data of the plurality of light receiving elements S using a different calculation technique. For example, the cumulative value of received light data obtained from each of the plurality of light receiving elements S may be calculated, and obtained as the received light intensity.

The received light data obtaining unit 13 obtains the received light data and the received light intensity for a preset predetermined period of time, to obtain time-series data D of the received light intensity for the predetermined period of time (step S5, NO). After the end of obtaining of the time-series data D (step S5, YES), the received light data obtaining unit 13 stores the time-series data D to the received light data storage unit 14 (step S6). Graphs shown in steps S4 and S5 of FIG. 4 show an example of the time-series data D. As can be seen from the graphs, the received light intensity varies periodically or regularly to draw the same waveform each time the rotating object 3 rotates one revolution. The variation in the received light intensity occurs irrespective of the number of revolutions of the rotating object 3. For example, even when the number of revolutions N0 of the rotating magnetic field is set to be high so that the rotating object 3 is rotated at high speed, time-series data D indicating the periodicity or regularity of the received light intensity can be obtained although the period of the waveform of the time-series data D decreases. Although, in the example of FIG. 4, time-series data D corresponding to about five revolutions of the rotating object 3 is shown, it is only necessary to obtain time-series data D corresponding to at least one revolutions of the rotating object 3. For example, the received light data obtaining unit 13 may be configured so that time-series data D corresponding to a different number of revolutions of the rotating object 3 can be obtained by changing the setting of the predetermined period of time for obtaining the received light data.

Next, the rotational speed calculation unit 15 reads the time-series data D from the received light data storage unit 14, and calculates the number of revolutions Na of the rotating object 3, according to an instruction to calculate from the general control unit 11 (step S7). Specifically, for example, as shown in step S7 of FIG. 4, a time T1 (sec) between adjacent troughs of the time-series data D, i.e., a time T1 it takes for the rotating object 3 to rotate one revolution, is measured. Thereafter, the rotational speed calculation unit 15 calculates the number of revolutions Na (rpm) of the rotating object 3 from the measured time T1 using a predetermined calculation expression shown in step S7 of FIG. 4. In this case, the time T1 may be measured for all sets of adjacent troughs of the time-series data D (four sets in the example of FIG. 4), and an average value of a plurality of the times T1, T1, . . . , and T1 may be used in calculation of the number of revolutions Na of the rotating object 3. Such a configuration allows for higher-precision calculation of the number of revolutions Na of the rotating object 3. Note that different time-series data D is obtained each time the viscosity η is measured, and therefore, measurement points may be appropriately set, depending on the waveform of the time-series data D. For example, as shown in step S7 of FIG. 4, instead of measuring a time between peak values of lower limits of the time-series data D, a time between peak values of upper limits of the time-series data D may be measured. Alternatively, a time between measurement points in the time-series data D having the same received light intensity value may be measured.

Next, the number of revolutions Na of the rotating object calculated by the rotational speed calculation unit 15 is output to the viscosity calculation unit 16. The viscosity calculation unit 16 reads the standard data stored in the standard data storage unit 17, and reads the number of revolutions N0 of the rotating magnetic field applied to the rotating object 3 from the rotation control unit 12, and then calculates the viscosity η of the sample 2A based on the standard data and the number of revolutions N0 of the rotating magnetic field, and the number of revolutions Na of the rotating object received from the rotational speed calculation unit 15, according to an instruction to calculate from the general control unit 11 (step S8). Specifically, the viscosity calculation unit calculates a difference ΔN (=N0−Na) in the number of revolutions between the number of revolutions N0 of the rotating magnetic field and the number of revolutions Na of the rotating object 3, and then calculates the slope ΔN/Na of the first-order equation from the number-of-revolutions difference ΔN and the number of revolutions Na of the rotating object 3, and then calculates the viscosity η (cP) of the sample 2A based on the slope ΔN/Na and the standard data. The viscosity η calculated by the viscosity calculation unit 16, and the number of revolutions Na of the rotating object 3 calculated by the rotational speed calculation unit 15, are automatically displayed together on the display unit 19 by the general control unit 11 (step S9). Note that, although not shown, after the end of the measurement of the viscosity η, the general control unit 11 stops outputting power to the light emitting unit 5 and the photodetector 6B to turn off the light emitting unit 5 and the photodetector 6B, and outputs an instruction to stop to the rotation control unit 12 to stop the rotation of the rotating object 3.

As described above, the viscosity measurement device 1 of the first embodiment is a practical implementation of measurement of the number of revolutions Na of the rotating object 3 using an optical means, that cannot be achieved in the prior art. Specifically, it is known that when a rough surface is illuminated with light, light waves reflected by different points on the rough surface interfere with each other, resulting in a random light spatial intensity distribution, so that a so-called "speckle pattern" is formed. The present inventors conceived, through trial and error, that the number of revolutions of the rotating object 3 could be readily detected by effective use of such a nature of the speckle. This conception encouraged the present inventors to create the uneven portion 3A on the rotating surface of the rotating object 3 that is a usually smooth curved surface, and to repeatedly analyze received light data while changing experimental conditions, such as the size of the uneven portion 3A and the like. As a result, the present inventors found that time-series data D obtained by emitting light to the rotating object 3 having the uneven portion 3A has certain periodicity or regularity, and by employing the above configuration according to the present invention, the number of revolutions Na of the rotating object 3 can be detected with high precision using the photodetector 6B that is commercially available and relatively inexpensive, etc. As a result, the rotational speed of the rotating object 3, which cannot be detected in the prior art without using an expensive image capture device, such as a high-speed camera, etc., can be detected by a simple control using the photodetector 6B that is commercially available and relatively inexpensive and the like. As a result, the manufacturing cost and size of the viscosity measurement device 1 can be significantly reduced while improving the precision of viscosity measurement.

[Second Embodiment]

Figure 5:
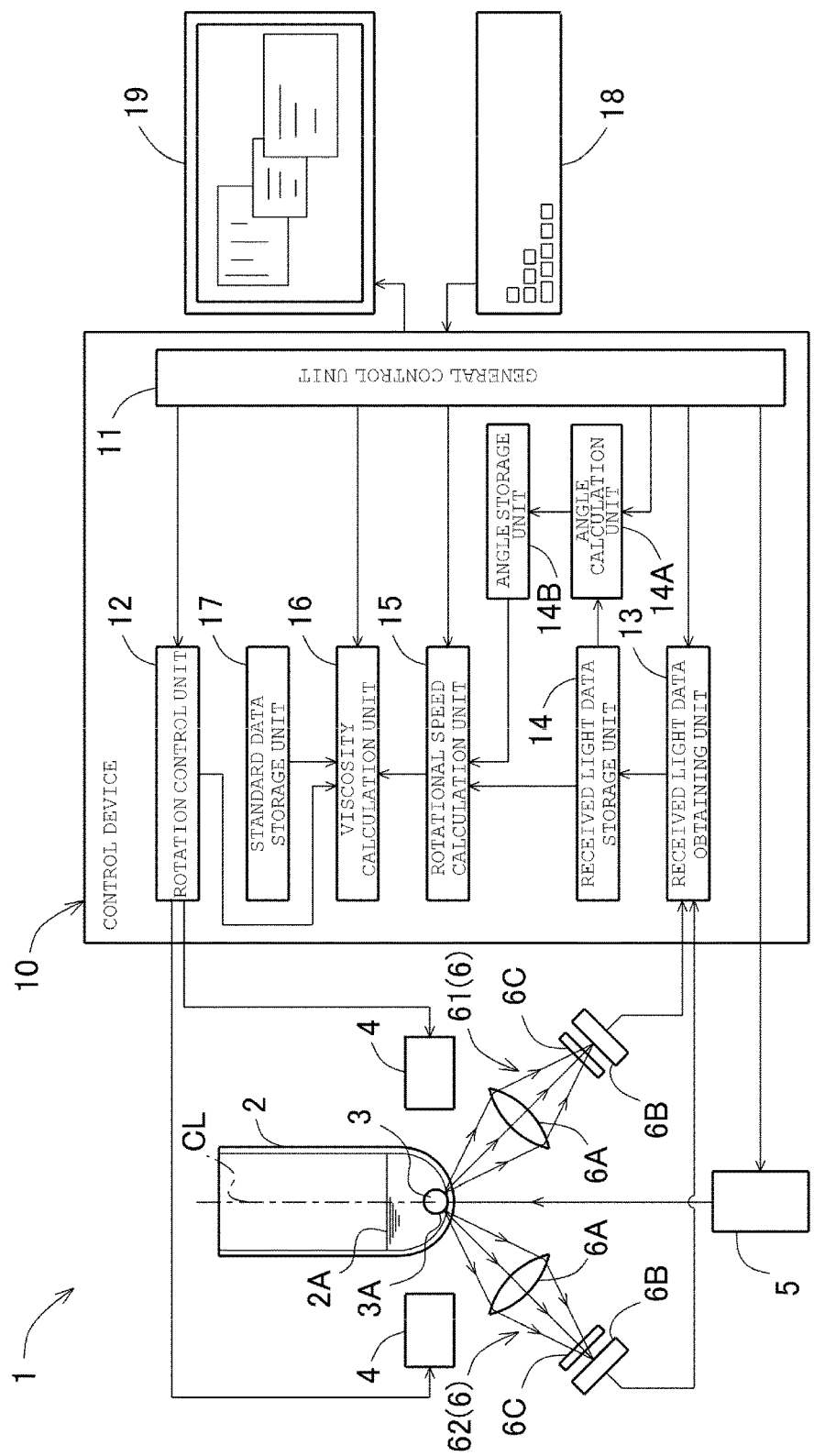
FIG. 5 is a block diagram showing an entire structure of a viscosity measurement device according to a second embodiment.
Figure 6:
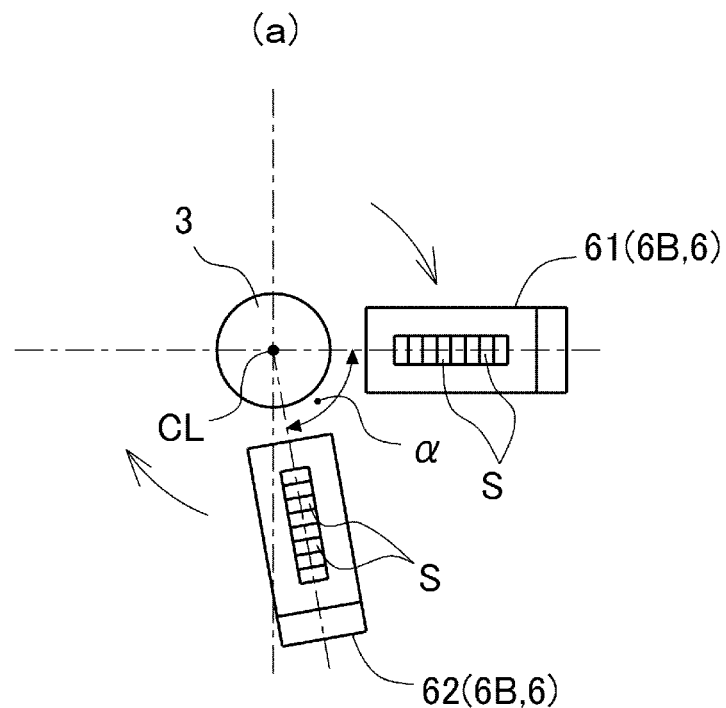
FIG. 6(*a*) is a plan view of a photodetector, and FIG. 6(*b*) is a plan view of a photodetector according to a variation of the second embodiment.
Figure 6:
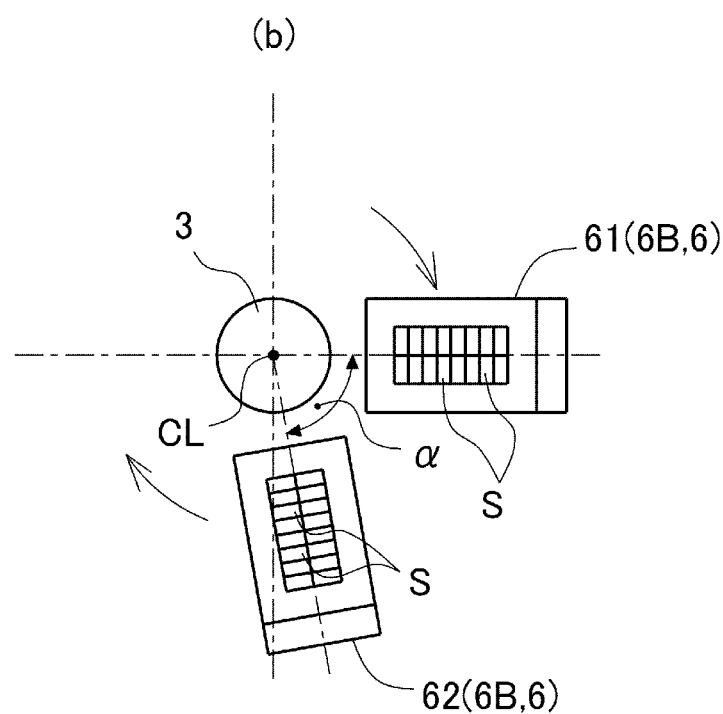
Figure 7:
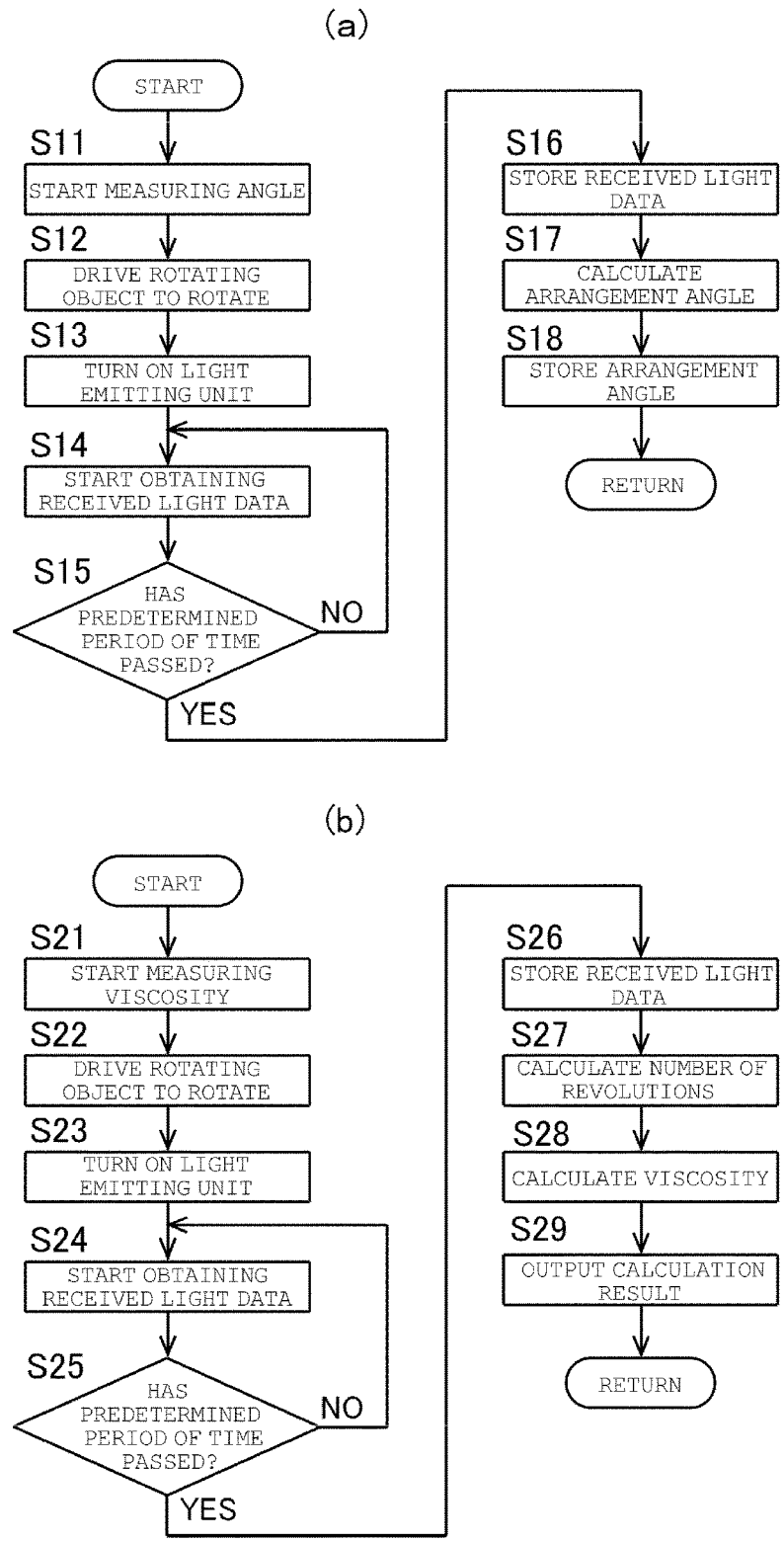
FIG. 7(*a*) is a flowchart showing details of an arrangement angle calculation control, and FIG. 7(*b*) is a flowchart showing details of a viscosity measurement control.

A viscosity measurement device 1 according to a second embodiment will be described with reference to FIGS. 5-10. In the second embodiment, shown is an example application of the rotational speed detection device of the present invention to calculation of an arrangement angle α and calculation of the viscosity η by the viscosity measurement device 1. Note that parts common to the first and second embodiments will not be described, and only parts different from the first embodiment will be described. As shown in FIG. 5, in the second embodiment, the light receiving unit 6 includes an upstream light receiving unit 61 provided upstream in the direction of rotation of the rotating object 3, and a downstream light receiving unit 62 provided downstream in the direction of rotation of the rotating object 3. The upstream light receiving unit 61 and the downstream light receiving unit 62 each include a lens 6A, a photodetector 6B, and a filter 6C.

As shown in FIG. 6(a), the photodetector 6B of the upstream light receiving unit 61 and the photodetector 6B of the downstream light receiving unit 62 are away from each other at an arrangement angle α around the rotation axis CL of the rotating object 3. Although, in FIG. 6(a), the arrangement angle α is set to an angle slightly smaller than 90 degrees, the arrangement angle α may be set to a small angle so that the two photodetectors 6B are close to each other.

Conversely, the arrangement angle α may be set to a large angle so that the two photodetectors 6B are provided on opposite sides of the rotational axis CL of the rotating object 3. As in the first embodiment, the photodetectors 6B of the upstream and downstream light receiving units 61 and 62 include a one-dimensional photodetector (e.g., a one-dimensional photodiode array, etc.) having a plurality of light receiving elements S arranged in parallel. The plurality of light receiving elements S have a light receiving surface facing the rotating surface of the rotating object 3 illuminated with light. In addition, the plurality of light receiving elements S are aligned in a direction perpendicular to the direction of rotation of the rotating object 3.

FIG. 6(b) shows a variation of the second embodiment. As shown in FIG. 6(b), the photodetector 6B is not limited to the one-dimensional photodetector of FIG. 6(a), and may be a two-dimensional photodetector having a plurality of light receiving elements S two-dimensionally arranged in parallel. In the photodetector 6B of FIG. 6(b), the plurality of light receiving elements S have a light receiving surface facing the rotating surface of the rotating object 3 illuminated with light. In addition, the plurality of light receiving elements S are aligned in the direction of rotation of the rotating object 3 and in a direction perpendicular to the direction of rotation of the rotating object 3. Note that, in the photodetectors 6B of FIGS. 6(a) and (b), the plurality of light receiving elements S may all be configured to function as the light receiving unit 6. Alternatively, a portion of the plurality of light receiving elements S may be caused to function as the light receiving unit 6, and if a light receiving element S functioning as the light receiving unit 6 is out of order, another light receiving element S may be effectively utilized as a spare light receiving element S.

As shown in FIG. 5, the control device 10 further includes an angle calculation unit 14A that calculates the arrangement angle α between the photodetector 6B of the upstream light receiving unit 61 and the photodetector 6B of the downstream light receiving unit 62, and an angle storage unit 14B that stores the arrangement angle α calculated by the angle calculation unit 14A.

Figure 8:
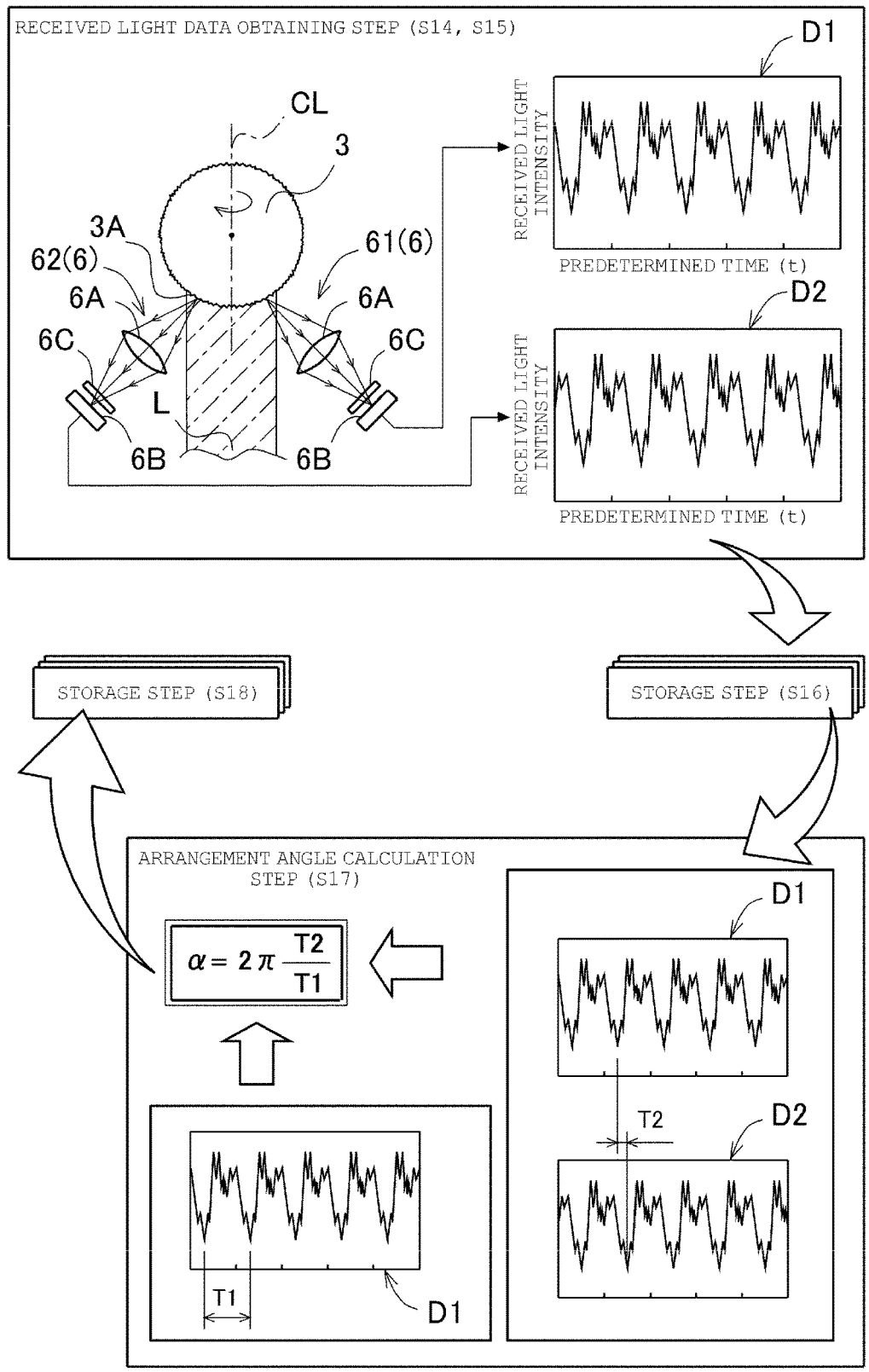
FIG. 8 is a diagram for describing details of an arrangement angle calculation control.

An arrangement angle calculation control performed by the control device 10 will be specifically described with reference to FIGS. 7(a) and 8 while referring to a procedure for operating the viscosity measurement device 1. The calculation of the arrangement angle α is performed when the viscosity measurement device 1 is adjusted before shipment or when the arrangement angle α is changed during maintenance of the photodetector 6B or the like. Initially, as a preliminary step for obtaining the arrangement angle, the worker places the sample 2A and the rotating object 3 together in the sample container 2, and sets the sample container 2 in the viscosity measurement device 1.

As shown in FIG. 7(a), after the end of the preliminary step, the worker operates the input unit 18 to input an instruction to start measuring the angle (step S11). Thereafter, the general control unit 11 outputs an instruction to rotate to the rotation control unit 12. The rotation control unit 12 performs a control so that the rotating magnetic field rotates at a number of revolutions of N0 specified by the general control unit 11 (step S12). When the rotating object 3 is driven to rotate, the general control unit 11 outputs power to the light emitting unit 5 to turn on the light emitting unit 5, which then starts emitting light to the rotating object 3 in the sample container 2 (step S13).

Next, the received light data obtaining unit 13 starts obtaining received light data output from the plurality of light receiving elements S of the photodetectors 6B, based on an instruction to obtain data from the general control unit 11 (step S14). The received light data obtaining unit 13 obtains the received light data from input data received from the photodetectors 6B at preset predetermined short time intervals. The received light data obtaining unit 13 calculates an average value of the received light data of the plurality of light receiving elements S at the predetermined short time intervals. The average value is obtained as the intensity of received light (reflected light intensity). The received light data obtaining unit 13 obtains the received light data and the received light intensity at the preset predetermined time intervals, to obtain time-series data D of the received light intensity within a predetermined period of time (step S15, NO). After the end of obtaining of the time-series data D (step S15, YES), the received light data obtaining unit 13 stores the time-series data D to the received light data storage unit 14 (step S16). The control process in the above steps S11-S16 are similar to that in steps S1-S6 of the first embodiment, except that, as shown in steps S14 and S15 of FIG. 8, in the second embodiment, the photodetector 6B of the upstream light receiving unit 61 and the photodetector 6B of the downstream light receiving unit 62 simultaneously obtain time-series data D1 and time-series data D2, respectively, as the time-series data D. Although, in the example of FIG. 8, the time-series data D1 and D2 corresponding to about five revolutions of the rotating object 3 is shown, the time-series data D1 and D2 corresponding to a different number of revolutions of the rotating object 3 may be obtained as in the first embodiment.

Next, the angle calculation unit 14A reads the time-series data D1 and D2 from the received light data storage unit 14 according to an instruction to calculate from the general control unit 11, and calculates the arrangement angle α between the photodetector 6B of the upstream light receiving unit 61 and the photodetector 6B of the downstream light receiving unit 62 (step S17). Specifically, for example, as shown in step S17 of FIG. 8, calculated are a time T1 (sec) between adjacent troughs of the time-series data D1, i.e., a time T1 it takes for the rotating object 3 to rotate one revolution, and a time T2 (sec) between a trough of the time-series data D1 and a trough of the time-series data D2 corresponding to that trough, i.e., a difference in detection time between the two photodetectors 6B. Note that the time T1 may be measured from the time-series data D2. Thereafter, the angle calculation unit 14A calculates the arrangement angle α between the photodetector 6B of the upstream light receiving unit 61 and the photodetector 6B of the downstream light receiving unit 62 from the measured times T1 and T2, using a predetermined calculation expression shown in step S17 of FIG. 8. The arrangement angle α calculated by the angle calculation unit 14A is stored in the angle storage unit 14B, and is used in calculation of an angular velocity ω of the rotating object 3 by the rotational speed calculation unit 15 (step S18). As a result, for example, even when the two photodetectors 6B are not accurately positioned, the arrangement angle α of the two photodetectors 6B can be accurately calculated by a simple operation. Note that, for example, when the arrangement angle α of the two photodetectors 6B can be accurately measured by the worker, or when the two photodetectors 6B can be accurately positioned using a jig or the like, the angle calculation unit 14A may be removed, and the measured or positioned arrangement angle α may be input to the angle storage unit 14B by the worker operating the input unit 18.

Figure 9:
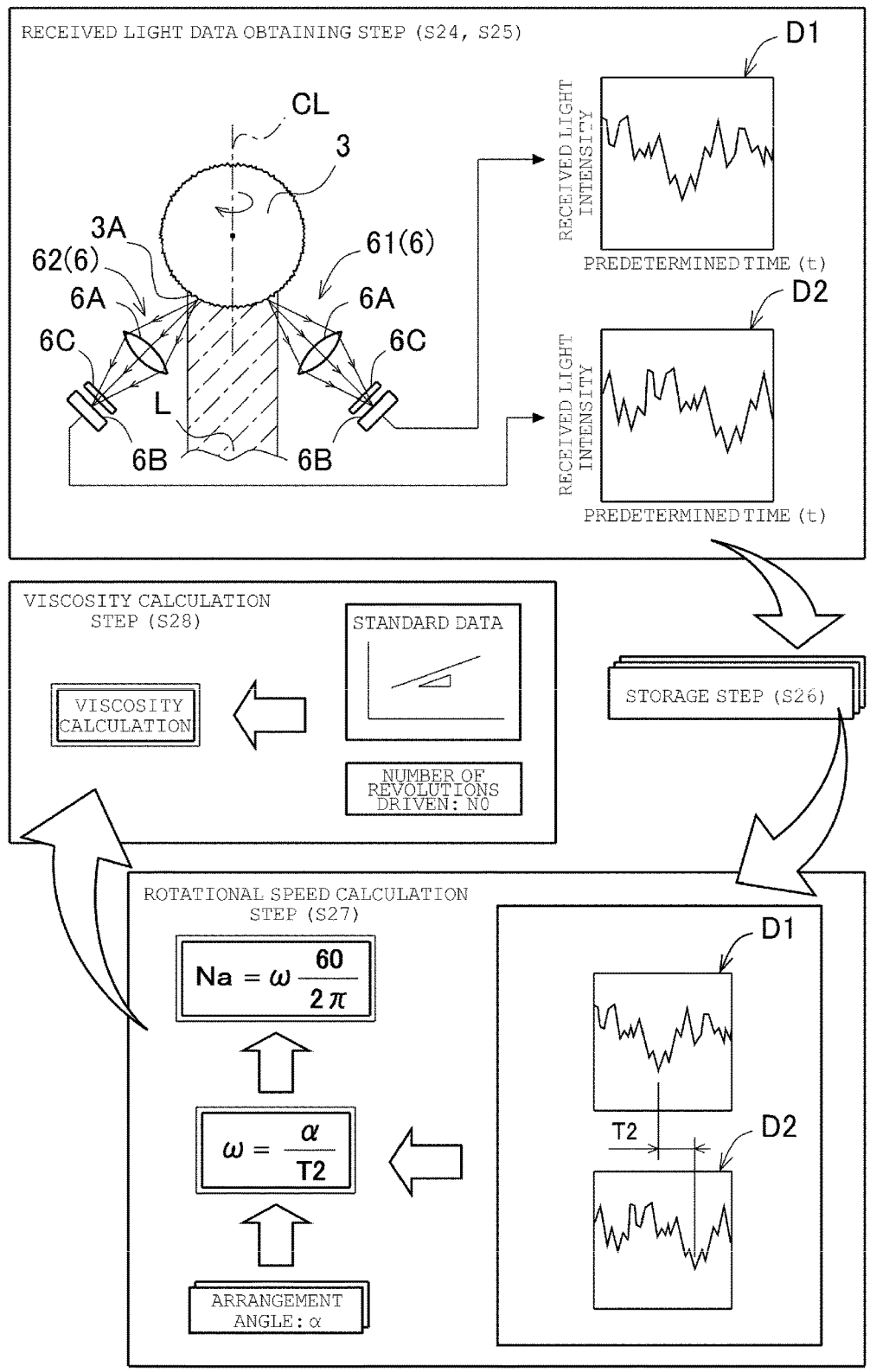
FIG. 9 is a diagram for describing details of a viscosity measurement control.

A rotational speed calculation control performed by the control device 10 will be specifically described with reference to FIGS. 7(b) and 9 while referring to a procedure of operating the viscosity measurement device 1. Initially, as a preliminary step for operating the viscosity measurement device 1, the measurer places the sample 2A whose viscosity η is to be measured, together with the rotating object 3, in the sample container 2, and sets the sample container 2 in the viscosity measurement device 1. As shown in FIG. 7(b), after the end of the preliminary step, the measurer operates the input unit 18 to input an instruction to start viscosity measurement (step S21), and then the general control unit 11 outputs an instruction to rotate to the rotation control unit 12, which then performs a control so that the rotating magnetic field rotates at a number of revolutions of N0 specified by the general control unit 11 (step S22). When the rotating object 3 is driven to rotate, the general control unit 11 outputs power to the light emitting unit to turn on the light emitting unit 5, which then starts emitting light to the rotating object 3 in the sample container 2 (step S23).

Next, the received light data obtaining unit 13 starts obtaining received light data output from the plurality of light receiving elements S of the photodetectors 6B, according to an instruction to obtain the data from the general control unit 11 (step S24). The received light data obtaining unit 13 obtains the received light data from input data received from the photodetectors 6B at preset predetermined short time intervals. The received light data obtaining unit 13 calculates an average value of the received light data from the plurality of light receiving elements S at the preset predetermined short time intervals, and obtains the average value as the intensity of reflected light (received light intensity). The received light data obtaining unit 13 obtains the received light data and the received light intensity for a preset predetermined period of time, to obtain time-series data D of the received light intensity for the predetermined period of time (step S25, NO). After the end of obtaining of the time-series data D (step S25, YES), the received light data obtaining unit 13 stores the time-series data D to the received light data storage unit 14 (step S26). The control process in the above steps S21-S26 are similar to that in steps S1-S6 of the first embodiment, except that, as shown in steps S24 and S25 of FIG. 9, in the second embodiment, the photodetector 6B of the upstream light receiving unit 61 and the photodetector 6B of the downstream light receiving unit 62 simultaneously obtain time-series data D1 and time-series data D2, respectively, as the time-series data D. Also, in the second embodiment, the predetermined period of time for which the received light data obtaining unit 13 obtains the received light data is set to be shorter than the predetermined period of time in the first embodiment. Graphs shown in steps S24 and S25 of FIG. 9 show an example of the time-series data D1 and D2. As can be seen from the graphs, the waveforms of the received light intensities of the time-series data D1 and D2 have periodicity or regularity, and vary with a time difference therebetween. Although, in the example of FIG. 9, the time-series data D1 and D2 corresponding to about half a revolution of the rotating object 3 is shown, it is only necessary to obtain the time-series data D1 and D2 corresponding to less than one revolution of the rotating object 3. For example, the received light data obtaining unit 13 may be configured so that the time-series data D1 and D2 corresponding to a different angle of rotation of the rotating object 3 may be obtained by changing the setting of the predetermined period of time for obtaining the received light data.

Next, the rotational speed calculation unit 15 reads the time-series data D1 and D2 from the received light data storage unit 14, and reads the arrangement angle α from the angle storage unit 14B, to calculate the number of revolutions Na of the rotating object 3, according to an instruction to calculate from the general control unit 11 (step S27). Specifically, for example, as shown in step S27 of FIG. 9, measured is a time T2 (sec) between a trough of the time-series data D1 and a trough of the time-series data D2 corresponding to that trough, i.e., a difference in detection time of the two photodetectors 6B. Thereafter, the rotational speed calculation unit 15 calculates the angular velocity ω (rad/s) of the rotating object 3 from the measured time T2 and the arrangement angle α using two predetermined calculation expressions shown in step S27 of FIG. 9, and calculates the number of revolutions Na (rpm) of the rotating object 3 from the calculated angular velocity ω.

Next, the number of revolutions Na of the rotating object calculated by the rotational speed calculation unit 15 is output to the viscosity calculation unit 16. The viscosity calculation unit 16 reads the standard data stored in the standard data storage unit 17, and reads the number of revolutions N0 of the rotating magnetic field applied to the rotating object 3 from the rotation control unit 12, and calculates the viscosity η of the sample 2A based on the standard data and the number of revolutions N0 of the rotating magnetic field, and the number of revolutions Na of the rotating object 3 received from the rotational speed calculation unit 15 (step S28). Thereafter, the viscosity η calculated by the viscosity calculation unit 16, and the number of revolutions Na of the rotating object 3 calculated by the rotational speed calculation unit 15, are automatically displayed together on the display unit 19 by the general control unit 11 (step S29). Note that the calculation of the viscosity η is similar to that of the first embodiment, and therefore, will not be described in detail.

Figure 10:
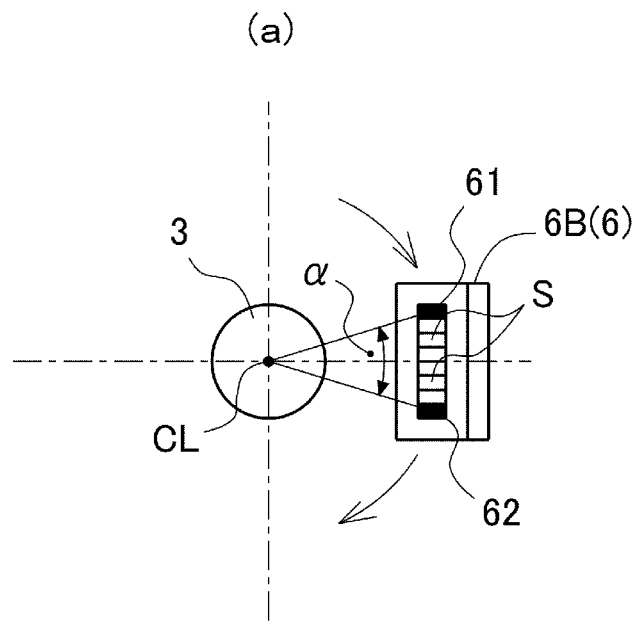
FIGS. 10(*a*) and 10(*b*) are plan views of a photodetector according to a variation of the second embodiment.
Figure 10:
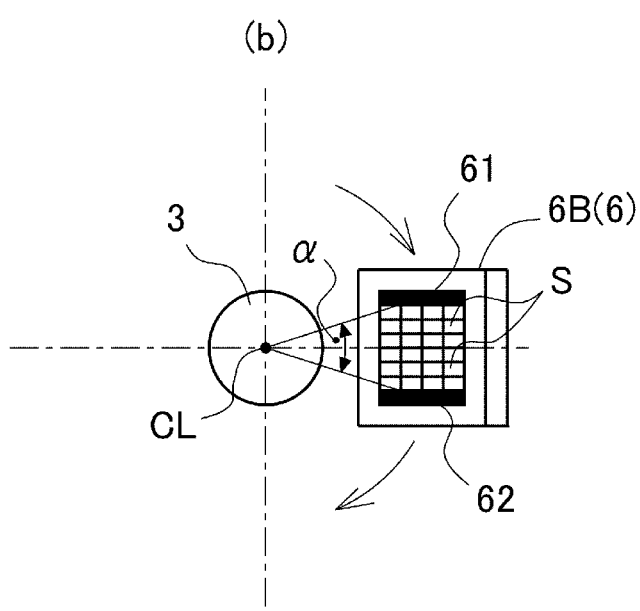

FIG. 10 illustrates another example of the second embodiment. Specifically, although, in the second embodiment, the upstream and downstream light receiving units 61 and 62 each include the lens 6A, the photodetector 6B, and the filter 6C, a single photodetector 6B may be configured to function as the upstream and downstream light receiving units 61 and 62 as shown in FIGS. 10(a) and 10(b). In this case, the lens 6A and the filter 6C included in the photodetector 6B are shared, so that the structure of the light receiving unit 6 can be simplified, resulting in a reduction in manufacturing cost. Details of FIGS. 10(a) and 10(b) will now be specifically described.

As shown in FIG. 10(a), the photodetector 6B includes a one-dimensional photodetector having a plurality of light receiving elements S arranged in parallel. In the photodetector 6B, the plurality of light receiving elements S have a light receiving surface facing the rotating surface of the rotating object 3 illuminated with light. In addition, the plurality of light receiving elements S are aligned in the direction of rotation of the rotating object 3. One of the plurality of light receiving elements S that is located most upstream in the direction of rotation functions as the upstream light receiving unit 61, and one of the plurality of light receiving elements S that is located most downstream in the direction of rotation functions as the downstream light receiving unit 62. Specifically, the control device 10 performs the arrangement angle calculation control shown in FIGS. 7(a) and 8 and the rotational speed calculation control of FIGS. 7(b) and 9, based on time-series data D1 obtained from the light receiving element S serving as the upstream light receiving unit 61 and time-series data D2 obtained from the light receiving element S serving as the downstream light receiving unit 62. Although, in the example of FIG. 10(a), the most upstream and downstream light receiving elements S function as the upstream and downstream light receiving units 61 and 62, the other light receiving elements S may function as the upstream and downstream light receiving units 61 and 62. Also, if the light receiving elements S functioning as the upstream and downstream light receiving units 61 and 62 are out of order, other light receiving elements S may be used as the upstream and downstream light receiving units 61 and 62. In this case, after the replacement, the arrangement angle α can be calculated by performing the arrangement angle calculation control of FIGS. 7(*a*) and 8 again. As a result, another light receiving element S may be effectively utilized as a spare light receiving element S.

Also, as shown in FIG. 10(*b*), the photodetector 6B may include a two-dimensional photodetector having a plurality of light receiving elements S two-dimensionally arranged in parallel. In the photodetector 6B of FIG. 10(*b*), the plurality of light receiving elements S have a light receiving surface facing the rotating surface of the rotating object 3 illuminated with light. In addition, the plurality of light receiving elements S are aligned in the direction of rotation of the rotating object 3 and in a direction perpendicular to the direction of rotation of the rotating object 3. A line of light receiving elements S located most upstream in the direction of rotation, of the plurality of light receiving elements S, functions as the upstream light receiving unit 61, and a line of light receiving elements S located most downstream in the direction of rotation, of the plurality of light receiving elements S, functions as the downstream light receiving unit 62. As a result, in addition to advantages similar to those of the one-dimensional photodetector of FIG. 10(*a*), the intensity of reflected light can be evaluated with high precision by obtaining time-series data D1 and D2 from received light data obtained from the plurality of light receiving elements S.

Thus, the viscosity measurement device 1 of the second embodiment has a further improvement to the viscosity measurement device 1 of the first embodiment. Specifically, when it is intended to measure the viscosity η of a relatively highly viscous substance, it is difficult for the rotating object to rotate due to viscous drag. In this case, when the rotational speed detection control of the first embodiment is used to detect one or more revolutions of the rotating object 3, it takes a time to obtain the time-series data D, and therefore, viscosity measurement cannot be quickly performed, which poses another problem. Therefore, in the second embodiment, by employing the above configuration of the present invention, the time-series data D1 and D2 of the upstream and downstream light receiving units 61 and 62 can be quickly obtained, resulting in quick viscosity measurement. In addition, the accurate arrangement angle α calculated by the arrangement angle calculation control can be used to calculate the number of revolutions Na of the rotating object 3 with high precision. As a result, the viscosity measurement precision of the viscosity measurement device 1 can be improved.

[Other Embodiments]

Figure 11:
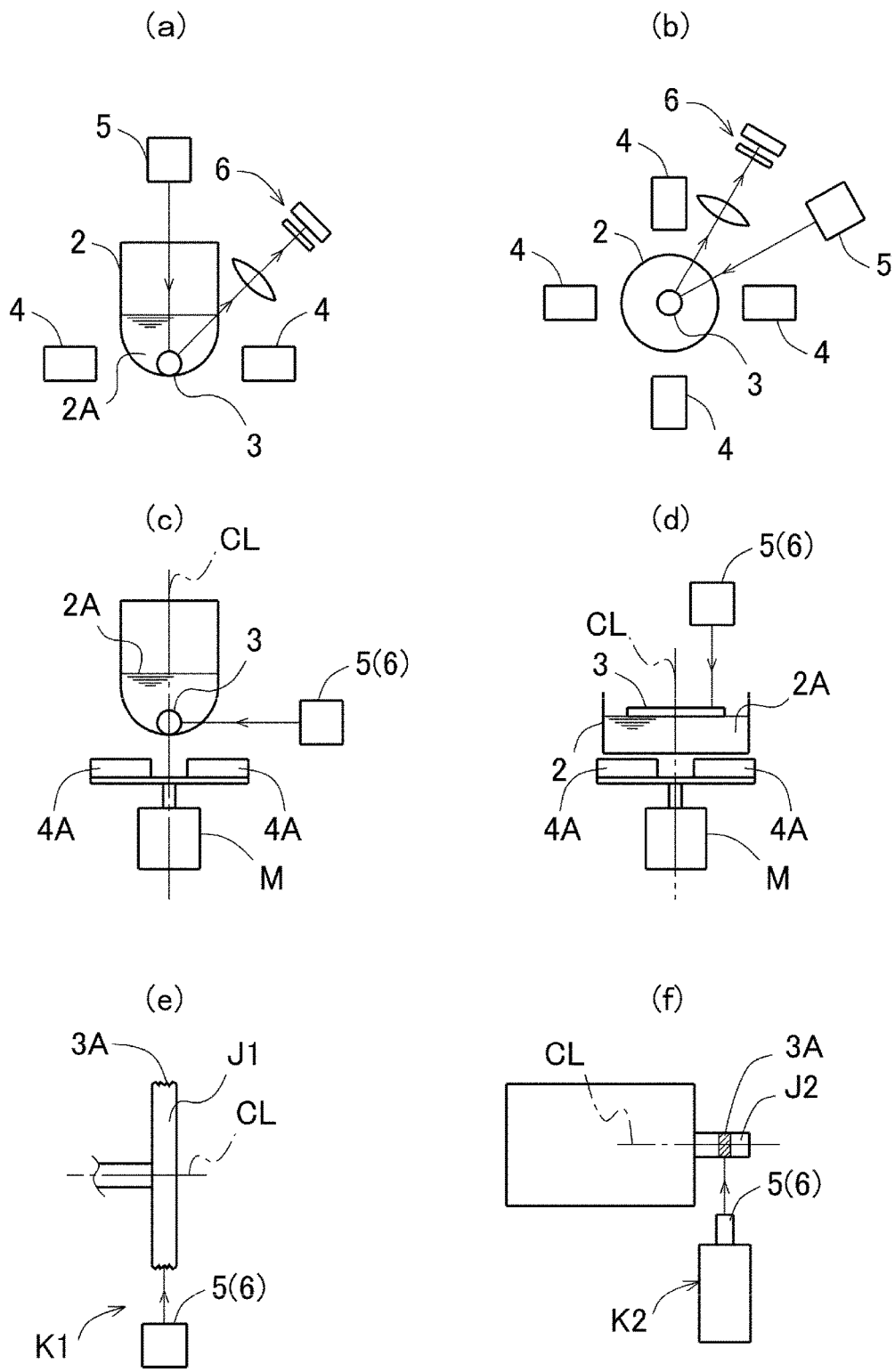
FIG. 11 is a diagram schematically showing rotational speed detection devices according to other embodiments.

(1) The arrangements of the light emitting unit 5 and the light receiving unit 6 with respect to the rotating object 3, that are shown in the first and second embodiments, are merely for illustrative purposes. Alternatively, for example, in order to reduce the size of the viscosity measurement device 1, the light emitting unit 5 and the light receiving unit 6 may be provided at different positions with respect to the rotating object 3. Specifically, for example, as shown in FIG. 11(*a*), the light emitting unit 5 may be provided directly above the rotating object 3 while the light receiving unit 6 may be provided above the electromagnets 4. Alternatively, for example, as shown in FIG. 11(*b*), the light emitting unit 5 and the light receiving unit 6 may be provided between the electromagnets 4 and 4 and at the same or substantially same height as that of the rotating object 3 and the electromagnets 4.

(2) The structures for applying the rotating magnetic field to the rotating object 3, that are shown in the first and second embodiments, are merely for illustrative purposes. Alternatively, for example, as shown in FIG. 11(*c*), the rotating magnetic field may be applied to the rotating object 3 by driving permanent magnets 4A provided below the rotating object 3 using a drive means, such as an electric motor M or the like, to rotate about the rotation axis CL. Also, in this case, as in (1), the light emitting unit 5 and the light receiving unit 6 may be provided at the same or substantially same height as that of the rotating object 3 as shown in FIG. 11(*c*), or alternatively, may be provided above or below the rotating object 3 although not shown.

(3) The structures of the rotating object 3 and the sample container 2 shown in the first and second embodiments are merely for illustrative purposes. Alternatively, the rotating object 3 and the sample container 2 may have other shapes or structures. Specifically, for example, as shown in FIG. 11(*d*), the sample container 2 may be a petri dish-shaped container, and the rotating magnetic field may be applied to a disc-shaped rotating object 3 floating on the surface of the sample 2A in the sample container 2. In this case, the uneven portion 3A may be formed on an upper surface, lower surface, or outer circumferential surface of the disc-shaped rotating object 3, and the number of revolutions Na of the rotating object 3 or the like may be detected using the light emitting unit 5 and the light receiving unit 6 that are provided above, below, or near an outer periphery of the rotating object 3. Note that FIG. 11(*d*) shows an example in which the uneven portion 3A is formed on an upper surface of the rotating object 3, and the light emitting unit 5 and the light receiving unit 6 are provided above the rotating object 3.

(4) In the first and second embodiments, in order to calculate the viscosity η using the viscosity calculation unit 16, the rotational speed calculation unit 15 is used to calculate the number of revolutions Na (rpm) of the rotating object 3, which is merely for illustrative purposes. The rotational speed as used herein encompasses both the number of revolutions and the angular velocity. For example, in the first embodiment, the rotational speed calculation unit 15 may calculate the angular velocity ω (rad/s) of the rotating object 3, and the viscosity calculation unit 16 may calculate the viscosity η using the angular velocity ω calculated by the rotational speed calculation unit 15 or using the number of revolutions Na calculated from the angular velocity ω. In the second embodiment, similarly, the viscosity calculation unit 16 may calculate the viscosity η using the angular velocity ω calculated by the rotational speed calculation unit 15 or using the number of revolutions Na calculated from the angular velocity ω.

(5) In the second embodiment, the rotational speed calculation control is performed using the time-series data D1 and D2 obtained from both of the upstream and downstream light receiving units 61 and 62, which is merely for illustrative purposes. In the entire configuration of the viscosity measurement device 1 shown in FIG. 5 of the second embodiment, time-series data D corresponding to one or more revolutions of the rotating object 3 may be obtained from one of the upstream and downstream light receiving units 61 and 62 so that the rotational speed calculation control shown in FIGS. 3 and 4 of the first embodiment can also be performed. Specifically, for example, when the viscosity η of a relatively high viscous substance is measured, the rotational speed calculation control of the second embodiment may be performed, and when the viscosity of a relatively low viscous substance is measured, the rotational speed calculation control of the first embodiment may be performed. Thus, the two rotational speed calculation controls of the first and second embodiments may both be performed. As a result, the advantages of the two rotational speed calculation controls can be utilized to measure the viscosity η with higher precision. In this case, for example, a control form changing unit (not shown) that changes the two rotational speed calculation controls may be provided in the control device 10 so that the two rotational speed calculation controls can be changed based on an input from the input unit 18 by the measurer or based on automatic determination by the control device 10.

(6) In the first and second embodiments, the rotational speed detection device of the present invention is applied to the viscosity measurement device 1, which is merely for illustrative purposes. In addition to the viscosity measurement device 1, the rotational speed detection device of the present invention may be applied to detection of a rotational speed by various devices. Specifically, for example, as shown in FIG. 11(e), in a rotation detector K1 that is used to detect the rotational speed of a rotating portion, such as a wheel shaft, output shaft, or the like, of a rotation drive unit of various vehicles, working machines, industrial machines, or the like, the uneven portion 3A may be formed on an outer circumferential surface of a cylindrical or disc-shaped rotating portion J1 (if the outer circumferential surface of the rotating portion J1 has a rough surface corresponding to the uneven portion 3A, the uneven portion 3A may not be formed), and the light emitting unit 5 and the light receiving unit 6 may be provided near an outer periphery of the rotating portion J1, and the rotational speed of the rotating portion J1 may be detected based on the principle of the rotational speed detection device of the present invention. In this case, it is not necessary to form regular projections and depressions (e.g., those possessed by a pulse encoder, etc.) on the outer circumferential surface of the rotating portion J1, advantageously leading to a reduction in manufacturing cost. Note that the uneven portion 3A may be formed on a side surface of the rotating portion J1, and the light emitting unit 5 and the light receiving unit 6 may be provided at a position facing the side surface of the rotating portion J1. Alternatively, for example, as shown in FIG. 11(f), in a mobile or stationary non-contact rotating meter K2 that is used to detect the rotational speed of a rotating portion, such as the rotating shafts of various rotating devices (e.g., motors, engines, fluid devices, etc.) or the like, the uneven portion 3A may be formed on an outer circumferential surface of a cylindrical or disc-shaped rotating portion J2 (if the outer circumferential surface of the rotating portion J2 has a rough surface corresponding to the uneven portion 3A, the uneven portion 3A may not be formed), and the rotational speed of the rotating portion J2 of various rotating devices may be detected based on the principle of the rotational speed detection device of the present invention. Also, in this case, the uneven portion 3A may be formed on a side surface (end surface) of the rotating portion J2, and the light emitting unit 5 and the light receiving unit 6 may be provided at a position facing the side surface of the rotating portion J2.

INDUSTRIAL APPLICABILITY

The rotational speed detection device and rotational speed detection method of the present invention are applicable to various devices that detect the rotational speed of a rotating object, in addition to the viscosity measurement device 1, the rotation detector K1, and the non-contact rotating meter K2.

REFERENCE SIGNS LIST

1 VISCOSITY MEASUREMENT DEVICE
2 SAMPLE CONTAINER
2A SAMPLE
3 ROTATING OBJECT
3A UNEVEN PORTION
4 ELECTROMAGNET
5 LIGHT EMITTING UNIT
6 LIGHT RECEIVING UNIT
6B PHOTODETECTOR
61 UPSTREAM LIGHT RECEIVING UNIT
62 DOWNSTREAM LIGHT RECEIVING UNIT
12 ROTATION CONTROL UNIT
13 RECEIVED LIGHT DATA OBTAINING UNIT
14A ANGLE CALCULATION UNIT
14B ANGLE STORAGE UNIT
15 ROTATIONAL SPEED CALCULATION UNIT
16 VISCOSITY CALCULATION UNIT
D TIME-SERIES DATA
D1 TIME-SERIES DATA
D2 TIME-SERIES DATA
N0 NUMBER OF REVOLUTIONS OF ROTATING MAGNETIC FIELD
Na NUMBER OF REVOLUTIONS OF ROTATING OBJECT
P1 DISTANCE BETWEEN TOP PORTIONS
P2 DISTANCE BETWEEN BOTTOM PORTIONS
S LIGHT RECEIVING ELEMENT
T1 TIME
T2 TIME
α ARRANGEMENT ANGLE
η VISCOSITY

The invention claimed is:
1. A rotational speed detection device comprising:
a rotating object;
a light emitting unit of emitting laser light to the rotating object;
a light receiving unit of receiving light reflected by the rotating object after being emitted from the light emitting unit to the rotating object, the light having a speckle pattern;
a received light data obtaining unit of obtaining received light data of the light received by the light receiving unit; and
a rotational speed calculation unit of calculating a rotational speed of the rotating object based on the received light data received by the received light data obtaining unit,
wherein
the rotating object is placed in a container of a transparent or translucent material capable of transmitting light, has a spherical shape having a radius of curvature smaller than the radius of curvature of a bottom inner surface of the container, has a rotating surface, and an irregular uneven portion on the rotating surface, the uneven portions having projections and depressions to generate a speckle pattern by interference of light reflected by different points on the uneven portions,
in the uneven portion, a distance between bottom portions of adjacent depressions and a distance between top portions of adjacent projections have a length that is one hundredth or less of a maximum perimeter of the rotating object, and is ten times or more a wavelength of the light emitted by the light emitting unit, the light emitting unit is positioned so that an optical axis of the laser light is substantially coaxial with a rotation axis of the rotating object, and is configured to emit the laser light to a circular region having a center at the rotation axis, the light receiving unit includes a single light receiving unit positioned to face a surface of the rotating object which is illuminated with the laser light, the received light data obtaining unit obtains time-series data of received light data of light reflected by the uneven portion, and received light intensity in the time-series data varies periodically to draw the same waveform each time the rotating object rotates one revolution, and the rotational speed calculation unit calculates the rotational speed of the rotating object from periodicity of the time-series data.

2. The rotational speed detection device of claim 1, wherein
the uneven portion is formed on the rotating surface of the rotating object by surface abrasion or polishing.

3. The rotational speed detection device of claim 1, wherein
the received light data obtaining unit obtains the time-series data corresponding to one or more revolutions of the rotating object, and
the rotational speed calculation unit measures a time it takes for the rotating object to rotate one revolution, from the time-series data corresponding to one or more revolutions of the rotating object, and calculates the rotational speed of the rotating object from the time.

4. The rotational speed detection device of claim 3, wherein
the light receiving unit has a plurality of light receiving elements facing the rotating surface of the rotating object illuminated by the light emitting unit, and aligned in a direction perpendicular to a direction of rotation of the rotating object, and
the received light data obtaining unit evaluates the overall received light data detected from the plurality of light receiving elements to obtain the time-series data.

5. The rotational speed detection device of claim 1, wherein
the rotational speed detection device further comprises a downstream light receiving unit provided downstream of the light receiving unit in a direction of rotation of the rotating object,
the received light data obtaining unit simultaneously obtains time-series data of the received light data of both the light receiving unit and the downstream light receiving unit, and
the rotational speed calculation unit calculates the rotational speed of the rotating object from the time-series data simultaneously obtained by both the light receiving unit and the downstream light receiving unit.

6. The rotational speed detection device of claim 5, wherein
the received light data obtaining unit obtains the time-series data corresponding to less than one revolution of the rotating object, and
the rotational speed calculation unit calculates the rotational speed of the rotating object from the time-series data corresponding to less than one revolution of the rotating object, and an arrangement angle of the light receiving unit and the downstream light receiving unit around the rotation axis of the rotating object.

7. The rotational speed detection device of claim 6, wherein
the rotational speed detection device has an angle calculation unit of calculating the arrangement angle, and an angle storage unit of storing the arrangement angle calculated by the angle calculation unit,
the received light data obtaining unit obtains the time-series data of the received light data corresponding to one or more revolutions of the rotating object, as time-series data for angle calculation,
the angle calculation unit calculates the arrangement angle from the time-series data for angle calculation, and
the rotational speed calculation unit calculates the rotational speed of the rotating object from the arrangement angle calculated by the angle calculation unit and stored in the angle storage unit.

8. The rotational speed detection device of claim 5, wherein
the light receiving unit and the downstream light receiving unit each receive light reflected by the rotating object after being emitted from the light emitting unit to the rotating object, without passing through a lens.

9. The rotational speed detection device of claim 5, wherein
the light receiving unit and the downstream light receiving unit each include a lens for imaging light reflected by the rotating object after being emitted to the rotating object, the lens being positioned to face a surface of the rotating object which is illuminated with the laser light, and a photodetector for detecting received light data of the imaged reflected light, the photodetector being positioned on an optical axis of the lens.

10. A viscosity measurement device including the rotational speed detection device of claim 1, the viscosity measurement device comprising:
a magnet for applying a rotating magnetic field to the rotating object from outside of the container;
a rotation control unit for controlling a rotational speed of the rotating magnetic field; and
a viscosity calculation unit for calculating a viscosity of a sample placed together with the rotating object in the container,
wherein
the viscosity calculation unit calculates the viscosity of the sample using the rotational speed of the rotating object calculated by the rotational speed calculation unit, and the rotational speed of the rotating magnetic field.

11. The rotational speed detection device of claim 1, wherein
the light receiving unit receives light reflected by the rotating object after being emitted from the light emitting unit to the rotating object, without passing through a lens.

12. A viscosity measurement device including the rotational speed detection device of claim 1, the viscosity measurement device comprising:
a magnet for applying a rotating magnetic field to the rotating object from outside of the container;
a rotation control unit for controlling a rotational speed of the rotating magnetic field; and
a viscosity calculation unit for calculating a viscosity of the a sample placed together with the rotating object in the container, wherein
the viscosity calculation unit calculates the viscosity of the sample using the rotational speed of the rotating object calculated by the rotational speed calculation unit, and the rotational speed of the rotating magnetic field, and the uneven portion is formed on the rotating surface of the rotating object by surface abrasion or polishing.

13. A rotational speed detection method for emitting laser light to a rotating object using a light emitting unit, receiving light reflected by the rotating object using a light receiving unit, the light having a speckle pattern, and calculating a rotational speed of the rotating object based on received light data of the light received by the light receiving unit, the method comprising:
- a preparation step of placing the rotating object in a container of a transparent or translucent material capable of transmitting light, the rotating object having a spherical shape having a radius of curvature smaller than the radius of curvature of a bottom inner surface of the container,
- a received light data obtaining step of emitting laser light to a circular region of the rotating object having a rotating surface and an irregular uneven portion on the rotating surface, the uneven portion having projections and depressions to generate a speckle pattern by interference of reflected light, a distance between bottom portions of adjacent depressions and a distance between top portions of adjacent projections having a length that is one hundredth or less of a maximum perimeter of the rotating object, and is ten times or more a wavelength of the light emitted by the light emitting unit, in such a manner that an optical axis of the laser light is substantially coaxial with a rotation axis of the rotating object, the circular region having a center at the rotation axis, and obtaining time-series data of received light data of light reflected by the uneven portion of the rotating object, using a single light receiving unit, received light intensity in the time-series data varying periodically to draw the same waveform each time the rotating object rotates one revolution; and
- a rotational speed calculation step of calculating the rotational speed of the rotating object from periodicity of the time-series data.

14. A rotating object used in the rotational speed detection method of claim 13, wherein
in the uneven portion, a distance between bottom portions of adjacent depressions and a distance between top portions of adjacent projections have a length that is one hundredth or less of a maximum perimeter of the rotating object, and is ten times or more a wavelength of the light emitted by the light emitting unit.

* * * * *